(12) United States Patent
Fournier et al.

(10) Patent No.: US 10,239,946 B2
(45) Date of Patent: Mar. 26, 2019

(54) CELL LINE OVEREXPRESSING HUMAN CD303 ANTIGEN

(71) Applicant: Laboratoire Francais du Fractionnement et des Biotechnologies, Les Ulis (FR)

(72) Inventors: Nathalie Fournier, Erquinghem-Lys (FR); Christophe De Romeuf, Lambersart (FR)

(73) Assignee: LABORATOIRE FRANCAIS DU FRACTIONNEMENT ET DES BIOTECHNOLOGIES, Les Ulis (FR)

( * ) Notice: Subject to any disclaimer, the term of this patent is extended or adjusted under 35 U.S.C. 154(b) by 0 days.

(21) Appl. No.: 15/563,046

(22) PCT Filed: Mar. 31, 2016

(86) PCT No.: PCT/EP2016/056994
§ 371 (c)(1),
(2) Date: Sep. 29, 2017

(87) PCT Pub. No.: WO2016/156449
PCT Pub. Date: Oct. 6, 2016

(65) Prior Publication Data
US 2018/0066060 A1 Mar. 8, 2018

(30) Foreign Application Priority Data
Mar. 31, 2015 (FR) ..................................... 15 52757

(51) Int. Cl.
C12N 15/85 (2006.01)
C07K 16/28 (2006.01)
C12N 15/79 (2006.01)

(52) U.S. Cl.
CPC .......... C07K 16/2851 (2013.01); C12N 15/79 (2013.01); C07K 2317/14 (2013.01); C07K 2317/24 (2013.01); C07K 2317/52 (2013.01); C07K 2317/54 (2013.01); C07K 2317/55 (2013.01); C07K 2317/56 (2013.01); C07K 2317/565 (2013.01); C07K 2317/567 (2013.01); C07K 2317/622 (2013.01); C07K 2317/732 (2013.01); C07K 2317/734 (2013.01); C07K 2317/76 (2013.01); C07K 2317/77 (2013.01); C07K 2317/92 (2013.01); C12N 2510/00 (2013.01)

(58) Field of Classification Search
None
See application file for complete search history.

(56) References Cited

FOREIGN PATENT DOCUMENTS

| | | |
|---|---|---|
| EP | 1176195 A1 | 1/2002 |
| JP | 2007044008 A | 2/2007 |
| WO | 1999051642 A1 | 10/1999 |
| WO | 2000042072 A2 | 7/2000 |
| WO | 2001077181 A3 | 3/2002 |
| WO | 2002060919 A2 | 8/2002 |
| WO | 2004029207 A2 | 4/2004 |
| WO | 2004063351 A2 | 7/2004 |
| WO | 2004074455 A2 | 9/2004 |
| WO | 2008028686 A2 | 3/2008 |
| WO | 2010045193 A1 | 4/2010 |
| WO | 2010106180 A2 | 9/2010 |
| WO | 2012041768 A1 | 4/2012 |
| WO | 2012080642 A1 | 6/2012 |
| WO | 2014093396 A1 | 6/2014 |
| WO | WO-2014093396 A1 * | 6/2014 ......... C07K 16/2851 |

OTHER PUBLICATIONS

Cao et al., PLoS Biol. Sep. 11, 2007;5(10):e248.*
Almagro et al., "Humanization of antibodies," Frontiers in Bioscience, vol. 13, pp. 1619-1633, Jan. 2008.
Cao et al., "BDCA2/Fc epsilon RI gamma complex signals through a novel BCR-like pathway in human plasmacytoid dendritic cells," PLoS Biology, vol. 5, No. 10, pp. 2190-2200, Oct. 2007.
Cardarelli et al., "A nonfucosylated human antibody to CD19 with potent B-cell depletive activity for therapy of B-Cell malignancies," Cancer Immunol. Immunother., vol. 59, pp. 257-265, 2010.
Cardarelli et al., "In vitro and In vivo Characterization of MDX-1401 for Therapy of Malignant Lymphoma," Clinical Cancer Research, vol. 15, pp. 3376-3383, Apr. 2009.
Dall'Acqua et al., "Increasing the Affinity of a Human IgG1 for the Neonatal Fc Receptor: Biological Consequences," The Journal of Immunology, vol. 169, pp. 5171-5180, 2002.
Dall'Acqua et al., "Modulation of the Effector Functions of a Human IgG1 through Engineering of Its Hinge Region," The Journal of Immunology, vol. 177, pp. 1129-1138, 2006.
Dall'Acqua et al., "Properties of Human IgG1s Engineered for Enhanced Binding to the Neonatal Fc Receptor (FcRn)," The Journal of Biological Chemistry, vol. 281, No. 33, pp. 23514-23524, Aug. 2006.
Dzionek et al., "BDCA-2, a novel plasmacytoid dendritic cell-specific type II C-type lectin, mediates antigen capture and is a potent inhibitor of interferon alpha-beta induction," The Journal of Experimental Medicine, vol. 194, No. 12, pp. 1823-1834, Dec. 2001.
Edelman et al., "The Covalent Structure of an Entire yG Immunoglobulin Molecule," Biochemistry, vol. 63, pp. 78-85, 1969.

(Continued)

Primary Examiner — Michael Szperka
(74) Attorney, Agent, or Firm — Potomac Law Group, PLLC

(57) ABSTRACT

The invention relates to a cell line expressing the gamma chain of the FcεRI receptor and human CD303 antigen, characterized in that said cell line is transfected in a stable manner by an expression vector comprising a nucleic acid molecule coding for human CD303 antigen and having strong expression of human CD303 on the surface thereof, e.g. at least 10000 molecules of human CD303 per cell, as well as a vector or vector kit that can be used to co-express the gamma chain of the FcεRI receptor and human CD303 antigen, and different uses of the cell line of the invention.

14 Claims, 9 Drawing Sheets

Specification includes a Sequence Listing.

(56) References Cited

OTHER PUBLICATIONS

Forthal et al., "Fc-Glycosylation Influences Fcγ Receptor Binding and Cell-Mediated Anti-HIV Activity of Monoclonal Antibody 2G12," The Journal of Immunology, vol. 185, pp. 6876-6882, Nov. 2010.
Herbst et al., "B-Cell Depletion In Vitro and In Vivo with an Afucosylated Anti-CD19 Antibody," The Journal of Pharmacology and Experimental Therapeutics, vol. 335, No. 1, pp. 213-222, 2010.
Hinton et al., "Engineered Human IgG Antibodies with Longer Serum Half-lives in Primates," The Journal of Biological Chemistry, vol. 279, No. 8, pp. 6213-6216, 2004.
Idusogie et al., "Engineered Antibodies with Increased Activity to Recruit Complement," J. Immunol., vol. 166, pp. 2571-2575, 2001.
Imai-Nishiya et al., "Double knockdown of alpha I,6-fucosyltransferase (FUT8) and GDP-mannose 4,6-dehydratase (GMD) in antibody-producing cells: a new strategy for generating fully non-fucosylated therapeutic antibodies with enhanced ADCC," BMC Biotechnology, vol. 7, No. 84, Nov. 2007.
International Search Report for International Application No. PCT/ER2016/056994 dated Jun. 7, 2016.
Jones et al., "Replacing the complementarity-determining regions in a human antibody with those from a mouse," Nature, vol. 321, pp. 522-525, May 1986.
Kanda et al., "Establishment of a GDP-mannose 4,6-dehydratase (GMD) knockout host cell line: A new strategy for generating completely non-fucosylated recombinant therapeutics," Journal of Biotechnology, vol. 130, pp. 300-310, 2007.
Lazar et al., "Engineered antibody Fc variants with enhanced effector function," PNAS, vol. 103, No. 11, pp. 4005-4010, Mar. 2006.
Maeda et al., "A Novel Plasmacytoid Dendritic Cell Line, CAL-1, Established from a Patient with Blastic Natural Killer Cell Lymphoma," International Journal of Hematology, vol. 81, pp. 148-154, 2005.
Moore et al., "Engineered Fc variant antibodies with enhanced ability to recruit complement and mediate effector functions," mAbs, vol. 2, Issue 2, pp. 181-189, Mar./Apr. 2010.
Mori et al., "Engineering Chinese Hamster Ovary Cells to Maximize Effecgtor Function of Produced Antibodies Using FUT8 siRNA," Biotechnology and Bioengineering, vol. 88, No. 7, pp. 901-908, Dec. 2004.
Olivier et al., "EB66 cell line, a duck embryonic stem cell-derived substrate fro the industrial production of therapeutic monoclonal antibodies with enhanced ADCC activity," mAbs vol. 2, No. 4, pp. 405-415, Aug. 2010.
Pellerin et al., "Anti-BDCA2 monoclonal antibody inhibits plasmacytoid dendritic cell activation through Fc-dependent and Fc-independent mechanisms," EMBO Molecular Medicine, vol. 7, No. 4, pp. 464-476, Mar. 2015.
Pellerin et al., "Table of Contents Supplementary Materials and Methods, Anti-BDCA2 monoclonal antibody inhibits plasmacytoid dendritic cell activation through Fc-dependent and Fc-independent mechanisms," EMBO Molecular Medicine, vol. 4, No. 7, Mar. 2015.
Riechmann et al., "Reshaping human antibodies for therapy," Nature, vol. 332, pp. 322-327, Mar. 1988.
Rock et al., "CD303 (BDCA-2) signals in dendritic cells via a BCR-like signalosome involving Syk, Slp65 and PLCc2," European Journal of Immunology, vol. 37, No. 12, pp. 3564-3575, Dec. 2007.
Shields et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry, vol. 216, No. 9, pp. 6591-6604, Mar. 2001.
Shields et al., "Lack of Fucose on Human IgG1 N-Linked Oligosaccharide Improves Binding to Human FcγRIII and Antibody-dependent Cellular Toxicity," The Journal of Biological Chemistry, vol. 277, No. 30, pp. 26733-26740, Jul. 1, 2002.
Shinkawa et al., "The absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," The Journal of Biological Chemistry, vol. 278, No. 5, pp. 3466-3473, Jan. 2003.
Suzuki et al., "A Nonfucosylated Anti-HER2 Antibody Augments Antibody-Dependent Cellular Cytotoxcity in Breast Cancer Patients," Clin. Cancer Res., vol. 13, pp. 1875-1882, Mar. 2007.
Umana et al., "Engineered glycoforms of an antineuro-blastoma IgG1 with optimized antibody-dependent cellular cytotoxcity activity," Nature Biotechnology, vol. 17, pp. 176-180, Feb. 1999.
Verhoeyen et al., "Reshaping Human Antibodies: Grafting an Antilysozyme Activity," Science, vol. 239, pp. 1534-1539, Mar. 1988.
Yamane-Ohnuki et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotechnology and Bioengineering, vol. 87, No. 5, pp. 614-622, Sep. 2004.

* cited by examiner

A

Clone 3C8 + G148

Week 2 anti-CD303 PE

Week 12 anti-CD303 PE

Clone 3C8 - G418

Week 2 anti-CD303 PE

Week 12 anti-CD303 PE

FIG. 11A
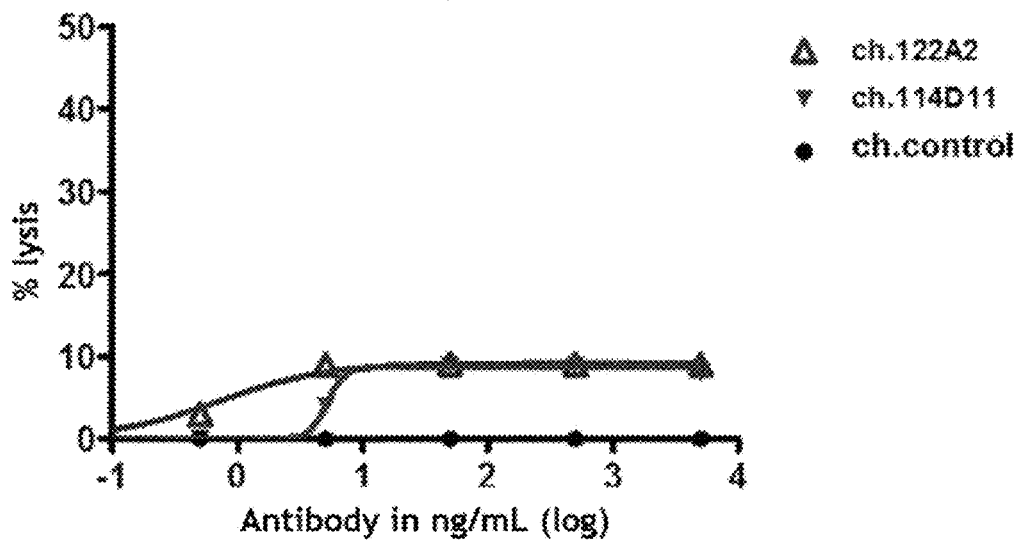
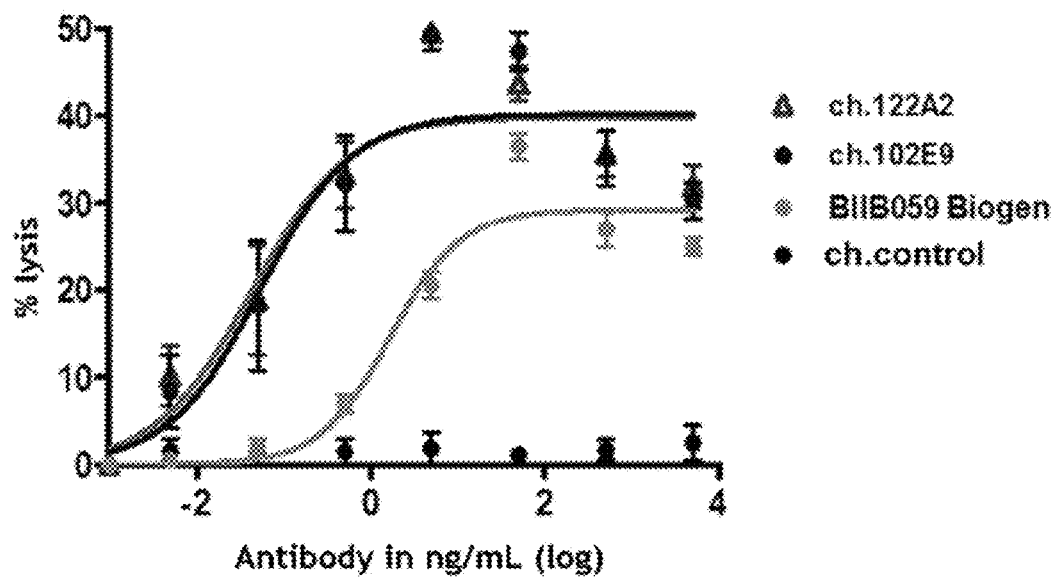
FIG. 11B ically an antibody against human CD303 antigen and effector

CELL LINE OVEREXPRESSING HUMAN CD303 ANTIGEN

FIELD OF THE INVENTION

The present invention relates to the field of cellular tools for characterizing the in vitro or in vivo activity of antibodies against human CD303 antigen, which may be used in the treatment or prevention of hematopoietic tumors derived from plasmacytoid dendritic cells (pDCs) or of inflammatory or autoimmune diseases involving pDCs. The invention relates in particular to cell lines expressing the gamma chain of Fcε receptor I (FcεRI) and human CD303 antigen, the line being stably transfected with an expression vector comprising a nucleic acid molecule encoding human CD303 antigen and having high expression of human CD303 on its surface.

PRIOR ART

Dendritic cells (called "DCs" throughout present description) are antigen-presenting cells (APCs) of the immune system. Under certain conditions, DCs have cytoplasmic projections similar to the dendrites of neurons.

Dendritic cells have two main functions:
  to trigger the adaptive immune response against "non-self" (foreign) antigens, by presenting these foreign antigens to T lymphocytes; and
  to maintain central tolerance to "self", by educating T lymphocytes in the thymus, by the so-called "negative selection" process.

DCs are capable of differentiating into various subpopulations, according to the stimuli they receive. There are three major types of DCs: conventional DCs, plasmacytoid DCs (called "pDCs") and inflammatory DCs.

Conventional DCs present self or non-self antigens in lymphoid organs or in the periphery. Inflammatory DCs, likely derived from blood monocytes, appear only in the event of stimulation following inflammation or infection.

Plasmacytoid DCs (pDCs) are circulating, round and without dendrites in the basal state, but acquire dendrites after activation, generally by a viral antigen. After stimulation, they produce a large amount of type I interferons (IFNs), and are chiefly involved in the antiviral response or in autoimmune diseases. Phenotypically, they are notably characterized by the following markers: CD4+, CD11c−, Lin−, CD303+, CD304+.

pDCs can be the cause of hematopoietic tumors in which they acquire an additional marker (CD56). These are referred to as blastic plasmacytoid dendritic cell neoplasm (BPDCN). These are also referred to as CD4+CD56+ hematopoietic tumors. These hematopoietic tumors are rare (1% of acute leukemias) and appear as cutaneous nodules associated with lymphadenopathy or swelling of the spleen and with frequent cytopenia. Cutaneous manifestations are very quickly followed by infiltration of the bone marrow. It is now accepted that the hematopoietic cells at the origin of these tumors are pDCs.

It has been proposed in WO2012/080642 to use anti-BDCA-2 (i.e., anti-CD303) antibodies to treat these neoplasms by tumor cell depletion.

pDCs are also involved in certain inflammatory diseases, and notably in certain autoimmune diseases, in particular via their secretion of type I IFN.

However, in order to treat these diseases effectively, it is necessary to have suitable monoclonal antibodies that allow, in humans, the most efficient as possible removal of pDCs.

To this end, there is a need for chimeric or humanized antibodies with high affinity for CD303 antigen and with effector capabilities (ADCC, CDC, phagocytosis, signaling via cross-linking of CD303 by Fc receptors, in particular Fcγ receptor IIIa (FcγRIIIa, also called CD16a) and/or apoptosis), thus enabling them to remove pDCs in physiological conditions.

Currently, due to limited access to patients' cells, and in order to guarantee reproducibility of the tests, characterization of the efficacy of anti-CD303 antibodies in vitro and in vivo is generally carried out on cell lines such as CAL-1 or equivalent, derived from cells from a human BPDCN patient.

However, the inventors noticed that the available lines express only a low number of CD303 molecules present on their surface, lower than that of most tumor cells from BPDCN patients, and that as a result these cell lines have only low discriminatory power with respect to anti-CD303 antibodies. Indeed, when the antigen density is too low, the functional activity of the antibodies is too low to be able to demonstrate differences in efficacy between different antibodies.

There is thus a real need to make available new cell lines stably expressing human CD303 antigen on their surface, and notably cell lines having increased discriminatory power so as to be able to select the anti-CD303 antibodies having the highest activity.

SUMMARY OF THE INVENTION

According to a first aspect, the present invention relates to a cell line expressing the gamma chain of Fcε receptor I (FcεRI) and human CD303 antigen, characterized in that said cell line is stably transfected with an expression vector comprising a nucleic acid molecule encoding human CD303 antigen and has high expression of CD303 on its surface.

According to a second aspect, the invention consists of an expression vector comprising a first nucleic acid molecule encoding human CD303 antigen and a second nucleic acid molecule encoding the gamma chain of human FcεRI.

According to a third aspect, the present invention is a kit comprising two expression vectors each comprising a nucleic acid molecule encoding human CD303 antigen and the gamma chain of human FcεRI, respectively.

According to a fourth aspect, the invention relates to the use of the cell line according to the invention to characterize a functional activity of an antibody against human CD303 antigen, preferably an activity of the ADCC, cytokine secretion, CDC, apoptosis or phagocytosis type, or to compare the binding affinity of several anti-CD303 antibodies to human CD303 antigen or the epitopes of human CD303 antigen recognized by several anti-CD303 antibodies.

According to a fifth aspect, the invention relates to a method for testing the ADCC activity of an antibody against human CD303 antigen, comprising the following steps:
  a) contacting the cell line according to the invention with an antibody against human CD303 antigen and effector cells;
  b) incubating for a suitable time to allow lysis of the cells of the cell line according to the invention of step a); and
  c) measuring the degree of lysis of the cells of the cell line according to the invention of step a).

According to a sixth aspect, the invention consists of a kit for characterizing anti-CD303 antibodies comprising the cell line according to the invention, and advantageously at least one reagent selected from effector cells, polyvalent IgG, and reference anti-CD303 antibodies.

DESCRIPTION OF THE FIGURES

FIG. 11. ADCC activity via CD16a induced by chimeric anti-CD303 antibodies 122A2, 114D1, or 102E9, by a control chimeric antibody or by humanized anti-CD303 antibody BIIB059 in the presence of the CAL-1 line not transfected with an expression vector for human CD303 antigen (A) or of clone NF-3C8 obtained after transfection of the CAL-1 line with an expression vector for human CD303 antigen, selection and cloning (B).

DETAILED DESCRIPTION OF THE INVENTION

Figure 1:
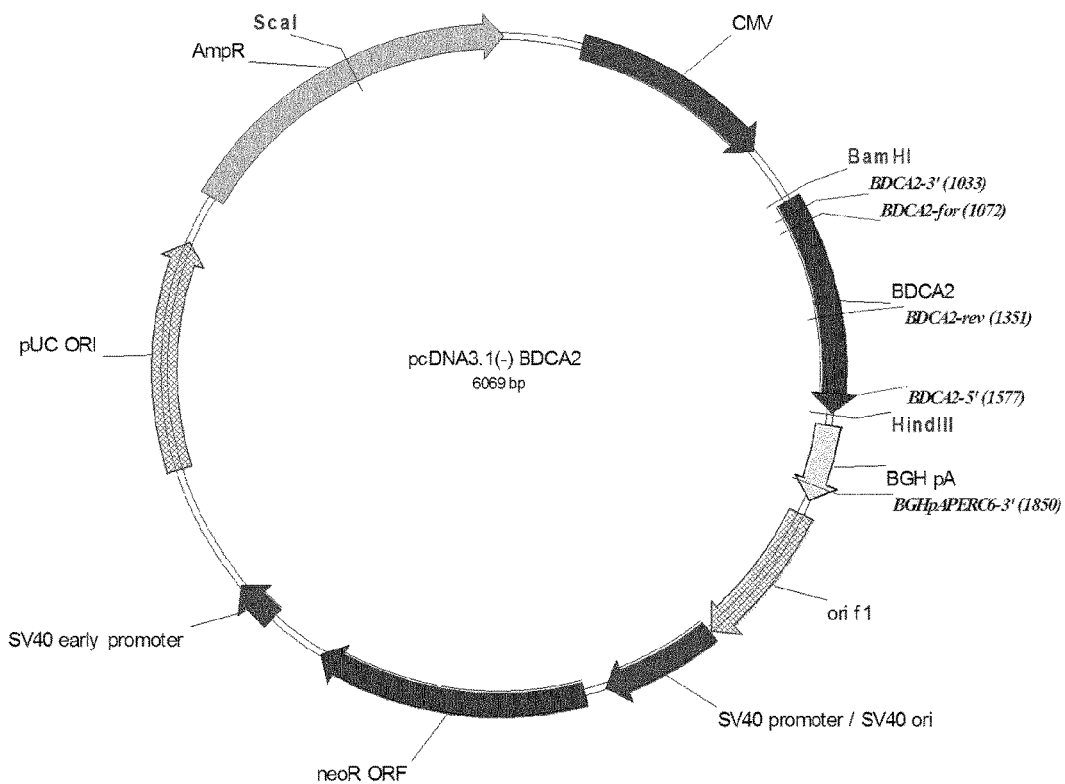
FIG. 1. Map of the vector pcDNA3.1(−).

Cell Line Expressing the Gamma Chain of Fcε Receptor I (FcεRI) and Human CD303 Antigen, Stably Transfected with an Expression Vector Comprising a Nucleic Acid Molecule Encoding Human CD303 Antigen and Having High CD303 Expression on its Surface The present invention relates to a cell line expressing the gamma chain of FcεRI and human CD303 antigen, characterized in that said cell line is stably transfected with an expression vector comprising a nucleic acid molecule encoding human CD303 antigen and has high CD303 expression on its surface.

Human CD303 antigen is C-type lectin domain family 4, member C (CLEC4), also called DLEC; HECL; BDCA2; CLECSF7; CLECSF11; or PRO34150 (see the Entrez Gene website for the CLEC4 gene). It is a type II transmembrane glycoprotein of 213 amino acids, comprising a short cytoplasmic domain with no evident signaling motif (amino acids 1-21), a transmembrane region (amino acids 22-41), a neck domain (amino acids 42-82), and a carbohydrate recognition extracellular domain (CRD; amino acids 83-213) (Dzionek et al.—2001). The mRNA sequence encoding this protein may be found in the 14 Feb. 2002 version of the GenBank database under accession number AF293615.1 (SEQ ID NO: 1), while the amino acid sequence is accessible in the 14 Feb. 2002 version of the GenBank database under accession number AAL37036.1 (SEQ ID NO: 2).

The inventors noted that in order to obtain a cell line stably expressing human CD303 antigen on its surface, it was essential that the cell line express the gamma chain of human FcεRI. Thus, for a cell line not originally expressing this gamma chain of human FcεRI, co-transfection of the cell line with an expression vector comprising a nucleic acid molecule encoding human CD303 antigen and another expression vector comprising a nucleic acid molecule encoding the gamma chain of human FcεRI, or transfection with a vector comprising two nucleic acid molecules, one encoding the gamma chain of human FcεRI and the other encoding human CD303 antigen, is necessary to obtain a cell line stably expressing human CD303 antigen on its surface. Conversely, if the original line already expresses the gamma chain of human FcεRI, transfection of a single expression vector comprising a nucleic acid molecule encoding human CD303 antigen is sufficient.

The sequence encoding the gamma chain of human FcεRI is known to a person skilled in the art. Notably, the mRNA sequence encoding this protein may be found in the 3 May 2014 version of the GenBank database under accession number NM_004106.1 (SEQ ID NO: 3), while the amino acid sequence is accessible in the 3 May 2014 version of the GenBank database under accession number NP_004097.1 (SEQ ID NO: 4). On this basis, a person skilled in the art will know how to design nucleic sequences encoding the gamma chain of human FcεRI capable of being inserted into an expression vector suitable for transfection of a cell line.

Origin of the Cell Line

The cell line according to the invention may be derived from any suitable cell line. Such a cell line is preferably a mammalian cell line, and even more preferably a human cell line. Among the cell lines that can be used to generate a line according to the invention, mention may be made notably of the following common lines: SP2/0; YB2/0; IR983F; human myeloma Namalwa; PERC6; CHO cell lines, notably CHO-K1, CHO Pro-5, CHO dhfr−, Wil-2; Jurkat; Vero; Molt-4; COS-7; 293-HEK; BHK; K6H6; NSO; SP2/0-Ag 14, and P3X63Ag8.653.

If the cell line expresses the gamma chain of human FcεRI, transfection of a single expression vector comprising a nucleic acid molecule encoding human CD303 antigen is sufficient to generate a cell line according to the invention. Otherwise, co-transfection of the cell line with a first expression vector comprising a nucleic acid molecule encoding human CD303 antigen and with another expression vector comprising a nucleic acid molecule encoding the gamma chain of human FcεRI, or transfection with a vector comprising two nucleic acid molecules, one encoding the gamma chain of human FcεRI and the other encoding human CD303 antigen, is necessary to obtain a cell line. A person skilled in the art is capable of determining which cell line does or does not express the gamma chain of human FcεRI by means of routine experiments (notably quantitative PCR or antibody labeling).

According to a first advantageous embodiment of the invention, the cell line according to the invention may be a human plasmacytoid dendritic cell (pDC) line, stably transfected with an expression vector comprising a nucleic acid molecule encoding human CD303 antigen. Normally, pDCs naturally express the gamma chain of FcεRI, and human pDC lines thus do not need to be transfected with an expression vector comprising a nucleic acid molecule encoding the gamma chain of human FcεRI. Subject to confirmation of expression of the gamma chain of FcεRI, simple transfection with an expression vector comprising a nucleic acid molecule encoding human CD303 antigen is sufficient.

Advantageously, the cell line according to the invention is a CAL-1 line or an equivalent line stably transfected with a vector comprising a nucleic acid molecule encoding human CD303 antigen. Indeed, the CAL-1 cell line (Maeda T et al., Int J Hematol. 2005 February; 81(2):148-54) is a cell line naturally expressing the gamma chain of FcεRI, and which thus does not need to be transfected with an expression vector comprising a nucleic acid molecule encoding the gamma chain of human FcεRI.

The CAL-1 cell line is derived from cells from a human BPDCN patient (Maeda T et al., Int J Hematol. 2005 February; 81(2):148-54 and JP 5011520). CAL-1 cells are defined as pDCs of phenotype Lin$^-$HLA-DR$^+$CD11c$^-$CD123$^+$CD4$^+$CD56$^+$. The CAL-1 cell line was deposited under the Budapest Treaty by Nagasaki University (1-14 Bunkyo-machi, Nagasaki 852-8521, Japan) to the National Institute of Advanced Industrial Science and Technology, International Patent Organism Depositary, NITE, (Chuoudai 6, 1-1-1, Higashi, Tsukuba-shi, Ibaraki, Japan, FERM P-20595 on 15 Jul. 2005, under the name CAL-1), and was characterized in detail in patent JP 5011520.

Any other human pDC line, such as another line derived from BPDCN cells from a human patient according to the protocol used to obtain the CAL-1 line described in Maeda T et al., Int J Hematol. 2005 February; 81(2):148-54, may also be used to obtain a line according to the invention by stable transfection of a nucleic acid molecule encoding human CD303 antigen and selection of a suitable clone. The protocol for obtaining a human pDC line from BPDCN cells from a human patient comprises notably the following steps:

Primary malignant BPDCN cells are obtained from peripheral blood of a patient diagnosed with BPDCN according to the WHO classification. In particular, peripheral blood mononuclear cells (PBMCs) from the BPDCN patient are cultured in medium containing 10% fetal calf serum (FCS) and 2 mM L-glutamine, without recombinant IL-2, with the medium changed twice per week, and subjected to long-term culture (several weeks or months).

Surviving cells after long-term culture can then be cloned (for example by limiting dilution) to obtain a long-lasting cell line in culture.

Such cell lines obtained according to the protocol described above are regarded as "equivalent" to the CAL-1 line within the meaning of the present invention.

In a second advantageous embodiment of the invention, the cell line according to the invention is a human T lymphocyte cell line, stably transfected with an expression vector comprising a first nucleic acid molecule encoding human CD303 antigen and a second nucleic acid molecule encoding the gamma chain of human FcεRI, or with two expression vectors each comprising a nucleic acid molecule encoding human CD303 antigen and the gamma chain of human FcεRI, respectively. Indeed, for cell lines not naturally expressing the gamma chain of FcεRI, it appears essential to transfect said cell lines with a nucleic acid molecule encoding the gamma chain of human FcεRI in order to be able to obtain a cell line stably expressing CD303 antigen on its surface.

In this case, the cell line according to the invention may notably be a Jurkat line (Clone E6-1: ATCC® TIB-152™, ECACC 88042803; Neo Jurkat: ATCC® CRL-2898™ expressing a neomycin-resistance gene), stably transfected with an expression vector comprising a first nucleic acid molecule encoding human CD303 antigen and a second nucleic acid molecule encoding the gamma chain of human FcεRI, or with two expression vectors each comprising a nucleic acid molecule encoding human CD303 antigen and the gamma chain of human FcεRI, respectively. Other equivalent cell lines accessible to a person skilled in the art may also be used.

Obtaining the Cell Line

Any expression vector suitable for expression in the selected cell line may be used, and notably—in the case of a mammalian cell line or a human cell line such as the Jurkat cell line or the human pDC cell line CAL-1 or an equivalent cell line—any expression vector allowing expression in mammalian cells, as described below in the section concerning vectors or vector kits.

The expression vector(s) may then be transfected into the cell line of interest (notably a mammalian cell line or a human cell line such as the Jurkat cell line or a human pDC cell line) by any suitable technology known to a person skilled in the art, and notably by nucleofection as described in Example 1, or by any other suitable technology, for example by using liposomes, cationic polymers, cationic lipids, or by biolistics.

After transfection of a pool of cells, the cells actually expressing CD303 antigen on their surface can be sorted by flow cytometry. Advantageously, the expression vector comprising a nucleic acid molecule encoding human CD303 antigen also comprises a nucleic acid molecule encoding a selection marker (for example, an antibiotic-resistance gene), thus making it possible to guarantee maintenance of human CD303 antigen expression by the cell line over time by culturing in medium selecting for cells expressing the selection marker (medium with antibiotic in the case of an antibiotic-resistance gene). After one or more periods of selection in medium selecting for cells expressing the selection marker and one or more cell-sorting procedures, clones expressing human CD303 antigen and the gamma chain of human FcεRI may be obtained by limiting-dilution cloning. In the foregoing description, selection is based only on expression of human CD303 antigen. That is related to the fact that the gamma chain of human FcεRI appears necessary for maintenance of expression of human CD303 antigen on the cell surface. However, selection based on another selection marker present in the nucleic acid molecule encoding the gamma chain of human FcεRI may be added to guarantee co-expression of both proteins in the transfected cell line. Advantageously, the selected transfectants express CD303 in a manner representative of the CD303 expressed on normal pDCs and/or pDCs from patients with autoimmune diseases or with blastic plasmacytoid dendritic cell neoplasm (BPDCN).

It is possible to use a cell line already stably transfected with an expression vector (pcDNA4/TO, for example) for the gamma chain of human FcεRI, referred to as "Fc γ-chain" cell line, and to transfect it with another expression vector comprising a nucleic acid molecule encoding human CD303 antigen. This obviously applies to the Jurkat cell line which FcεRI γ-chain transfected form is called "Fc γ-chain Jurkat".

Number of CD303 Molecules Per Cell

The cell line according to the invention is stably transfected with an expression vector comprising a nucleic acid molecule encoding human CD303 antigen and has high expression of human CD303 antigen on its surface.

By "high expression of human CD303 antigen" is meant that the cell line according to the invention, which has been stably transfected with an expression vector comprising a nucleic acid molecule encoding human CD303 antigen, has a higher expression level of human CD303 antigen than that of the cell line before stable transfection with an expression vector comprising a nucleic acid molecule encoding human CD303 antigen. When the original cell line does not express CD303, the transfected line according to the invention necessarily meets this criterion if it expresses CD303 on its surface. When the original cell line already expresses CD303 (preferably at a low level), the expression level of human CD303 antigen of the transfected line according to the invention is advantageously at least 10%, at least 20%, at least 25%, at least 30%, at least 40%, at least 50%, at least 60%, at least 70%, at least 75%, at least 80%, at least 90%, at least 100% (amplification factor 2), at least 125%, at least 150%, at least 175%, at least 200% (amplification factor 3), at least 250%, at least 300% (amplification factor 4), at least 350%, at least 400% (amplification factor 5), at least 450%, at least 500% (amplification factor 6), at least 600% (amplification factor 7), at least 700% (amplification factor 8), at least 800% (amplification factor 9), at least 900% (amplification factor 10), indeed at least 1000% (amplification factor 11) higher than that of the line before stable transfection with an expression vector comprising a nucleic acid molecule encoding human CD303 antigen. The expression level may notably be expressed as the number of human CD303 antigen molecules per cell.

The number of human CD303 antigen molecules per cell can be determined by flow cytometry—notably using the QIFIKIT (Dako), which makes it possible to determine the number of antigenic sites per cell ranging between 1,000 and 1,000,000—and murine anti-(human CD303) antibodies. The principle of the test is as follows:

Cells are labeled with primary mouse monoclonal antibody against human CD303 antigen. In a separate test tube, cells are labeled with irrelevant primary mouse monoclonal antibody (control). Then, cells and set-up beads and calibration beads of the kit are labeled, in parallel, with fluorescein-conjugated anti-mouse secondary antibody.

The primary antibody used for labeling of the cells is used at saturating concentration. The saturation conditions are determined by performing titration studies of each primary mouse monoclonal antibody using the fluorescein-conjugated anti-mouse secondary antibody. The primary antibody may be any mouse IgG isotype. Under these conditions, the number of bound primary antibody molecules corresponds to the number of antigenic sites present on the cell surface.

The secondary antibody is also used at saturating concentration. Consequently, the fluorescence is correlated with the number of bound primary antibody molecules on the cells and on the beads. The samples are then analyzed in the following order:

Tube 1 (set-up beads): This sample is used to establish window of analysis. The set-up beads comprise a mixture of blank beads (no antigenic sites) and beads expressing a high level of antigenic sites.

Tube 2 (calibration beads): This sample is used for the construction of the calibration curve (mean fluorescence intensity (MFI)) against antibody-binding capacity (ABC).

Cells are then analyzed on the flow cytometer and the antigen density on the cells (ABC value) is calculated based on the equation of the calibration curve.

Advantageously, the cell line has on its surface at least 10,000 human CD303 molecules per cell, preferably between 10,000 and 500,000, between 10,000 and 480,000, between 10,000 and 460,000, between 10,000 and 440,000, between 10,000 and 420,000, between 10,000 and 400,000, between 10,000 and 380,000, between 10,000 and 360,000, between 10,000 and 340,000, between 10,000 and 320,000, between 10,000 and 300,000, between 10,000 and 280,000, between 10,000 and 260,000, between 10,000 and 240,000, between 10,000 and 220,000, between 10,000 and 200,000, between 10,000 and 180,000, between 10,000 and 160,000, between 10,000 and 140,000, between 10,000 and 120,000, between 10,000 and 100,000, between 10,000 and 90,000, between 10,000 and 80,000, between 10,000 and 70,000, between 10,000 and 60,000, between 10,000 and 50,000, between 10,000 and 40,000, between 10,000 and 30,000, between 10,000 and 20,000, between 20,000 and 500,000, between 20,000 and 480,000, between 20,000 and 460,000, between 20,000 and 440,000, between 20,000 and 420,000, between 20,000 and 400,000, between 20,000 and 380,000, between 20,000 and 360,000, between 20,000 and 340,000, between 20,000 and 320,000, between 20,000 and 300,000, between 20,000 and 280,000, between 20,000 and 260,000, between 20,000 and 240,000, between 20,000 and 220,000, between 20,000 and 200,000, between 20,000 and 180,000, between 20,000 and 160,000, between 20,000 and 140,000, between 20,000 and 120,000, between 20,000 and 100,000, between 20,000 and 90,000, between 20,000 and 80,000, between 20,000 and 70,000, between 20,000 and 60,000, between 20,000 and 50,000, between 20,000 and 40,000, between 20,000 and 30,000, between 20,000 and 500,000, between 20,000 and 480,000, between 20,000 and 460,000, between 20,000 and 440,000, between 20,000 and 420,000, between 20,000 and 400,000, between 20,000 and 380,000, between 20,000 and 360,000, between 20,000 and 340,000, between 20,000 and 320,000, between 20,000 and 300,000, between 20,000 and 280,000, between 20,000 and 260,000, between 20,000 and 240,000, between 20,000 and 220,000, between 20,000 and 200,000, between 20,000 and 180,000, between 20,000 and 160,000, between 20,000 and 140,000, between 20,000 and 120,000, between 20,000 and 100,000, between 20,000 and 90,000, between 20,000 and 80,000, between 20,000 and 70,000, between 20,000 and 60,000, between 20,000 and 50,000, between 20,000 and 40,000, between 20,000 and 30,000, between 25,000 and 500,000, between 25,000 and 480,000, between 25,000 and 460,000, between 25,000 and 440,000, between 25,000 and 420,000, between 25,000 and 400,000, between 25,000 and 380,000, between 25,000 and 360,000, between 25,000 and 340,000, between 25,000 and 320,000, between 25,000 and 300,000, between 25,000 and 280,000, between 25,000 and 260,000, between 25,000 and 240,000, between 25,000 and 220,000, between 25,000 and 200,000, between 25,000 and 180,000, between 25,000 and 160,000, between 25,000 and 140,000, between 25,000 and 120,000, between 25,000 and 100,000, between 25,000 and 90,000, between 25,000 and 80,000, between 25,000 and 70,000, between 25,000 and 60,000, between 25,000 and 50,000, between 25,000 and 40,000, between 25,000 and 30,000, between 30,000 and 500,000, between 30,000 and 480,000, between 30,000 and 460,000, between 30,000 and 440,000, between 30,000 and 420,000, between 30,000 and 400,000, between 30,000 and 380,000, between 30,000 and 360,000, between 30,000 and 340,000, between 30,000 and 320,000, between 30,000 and 300,000, between 30,000 and 280,000, between 30,000 and 260,000, between 30,000 and 240,000, between 30,000 and 220,000, between 30,000 and 200,000, between 30,000 and 180,000, between 30,000 and 160,000, between 30,000 and 140,000, between 30,000 and 120,000, between 30,000 and 100,000, between 30,000 and 90,000, between 30,000 and 80,000, between 30,000 and 70,000, between 30,000 and 60,000, between 30,000 and 50,000, between 30,000 and 40,000, between 40,000 and 500,000, between 40,000 and 480,000, between 40,000 and 460,000, between 40,000 and 440,000, between 40,000 and 420,000, between 40,000 and 400,000, between 40,000 and 380,000, between 40,000 and 360,000, between 40,000 and 340,000, between 40,000 and 320,000, between 40,000 and 300,000, between 40,000 and 280,000, between 40,000 and 260,000, between 40,000 and 240,000, between 40,000 and 220,000, between 40,000 and 200,000, between 40,000 and 180,000, between 40,000 and 160,000, between 40,000 and 140,000, between 40,000 and 120,000, between 40,000 and 100,000, between 40,000 and 90,000, between 40,000 and 80,000, between 40,000 and 70,000, between 40,000 and 60,000, between 40,000 and 50,000, between 50,000 and 500,000, between 50,000 and 480,000, between 50,000 and 460,000, between 50,000 and 440,000, between 50,000 and 420,000, between 50,000 and 400,000, between 50,000 and 380,000, between 50,000 and 360,000, between 50,000 and 340,000, between 50,000 and 320,000, between 50,000 and 300,000, between 50,000 and 280,000, between 50,000 and 260,000, between 50,000 and 240,000, between 50,000 and 220,000, between 50,000 and 200,000, between 50,000 and 180,000, between 50,000 and 160,000, between 50,000 and 140,000, between 50,000 and 120,000, between 50,000 and 100,000, between 50,000 and 90,000, between 50,000 and 80,000, between 50,000 and 70,000, between 50,000 and 60,000, between 60,000 and 500,000, between 60,000 and 480,000, between 60,000 and 460,000, between 60,000 and 440,000, between 60,000 and 420,000, between 60,000 and 400,000, between 60,000 and 380,000, between 60,000 and 360,000, between 60,000 and 340,000, between 60,000 and 320,000, between 60,000 and 300,000, between 60,000 and 280,000, between 60,000 and 260,000, between 60,000 and 240,000, between 60,000 and 220,000, between 60,000 and 200,000, between 60,000 and 180,000, between 60,000 and 160,000, between 60,000 and 140,000, between 60,000 and 120,000, between 60,000 and 100,000, between 60,000 and 90,000, between 60,000 and 80,000, between 60,000 and 70,000, between 70,000 and 500,000, between 70,000 and 480,000, between 70,000 and 460,000, between 70,000 and 440,000, between 70,000 and 420,000, between 70,000 and 400,000, between 70,000 and 380,000, between 70,000 and 360,000, between 70,000 and 340,000, between 70,000 and 320,000, between 70,000 and 300,000, between 70,000 and 280,000, between 70,000 and 260,000, between 70,000 and 240,000, between 70,000 and 220,000, between 70,000 and 200,000, between 70,000 and 180,000, between 70,000 and 160,000, between 70,000 and 140,000, between 70,000 and 120,000, between 70,000 and 100,000, between 70,000 and 90,000, between 70,000 and 80,000, between 80,000 and 500,000, between 80,000 and 480,000, between 80,000 and 460,000, between 80,000 and 440,000, between 80,000 and 420,000, between 80,000 and 400,000, between 80,000 and 380,000, between 80,000 and 360,000, between 80,000 and 340,000, between 80,000 and 320,000, between 80,000 and 300,000, between 80,000 and 280,000, between 80,000 and 260,000, between 80,000 and 240,000, between 80,000 and 220,000, between 80,000 and 200,000, between 80,000 and 180,000, between 80,000 and 160,000, between 80,000 and 140,000, between 80,000 and 120,000, between 80,000 and 100,000, between 80,000 and 90,000, between 90,000 and 500,000, between 90,000 and 480,000, between 90,000 and 460,000, between 90,000 and 440,000, between 90,000 and 420,000, between 90,000 and 400,000, between 90,000 and 380,000, between 90,000 and 360,000, between 90,000 and 340,000, between 90,000 and 320,000, between 90,000 and 300,000, between 90,000 and 280,000, between 90,000 and 260,000, between 90,000 and 240,000, between 90,000 and 220,000, between 90,000 and 200,000, between 90,000 and 180,000, between 90,000 and 160,000, between 90,000 and 140,000, between 90,000 and 120,000, between 90,000 and 100,000, between 100,000 and 500,000, between 100,000 and 480,000, between 100,000 and 460,000, between 100,000 and 440,000, between 100,000 and 420,000, between 100,000 and 400,000, between 100,000 and 380,000, between 100,000 and 360,000, between 100,000 and 340,000, between 100,000 and 320,000, between 100,000 and 300,000, between 100,000 and 280,000, between 100,000 and 260,000, between 100,000 and 240,000, between 100,000 and 220,000, between 100,000 and 200,000, between 100,000 and 180,000, between 100,000 and 160,000, between 100,000 and 140,000, between 100,000 and 120,000, between 120,000 and 500,000, between 120,000 and 480,000, between 120,000 and 460,000, between 120,000 and 440,000, between 120,000 and 420,000, between 120,000 and 400,000, between 120,000 and 380,000, between 120,000 and 360,000, between 120,000 and 340,000, between 120,000 and 320,000, between 120,000 and 300,000, between 120,000 and 280,000, between 120,000 and 260,000, between 120,000 and 240,000, between 120,000 and 220,000, between 120,000 and 200,000, between 120,000 and 180,000, between 120,000 and 160,000, between 120,000 and 140,000, between 140,000 and 500,000, between 140,000 and 480,000, between 140,000 and 460,000, between 140,000 and 440,000, between 140,000 and 420,000, between 140,000 and 400,000, between 140,000 and 380,000, between 140,000 and 360,000, between 140,000 and 340,000, between 140,000 and 320,000, between 140,000 and 300,000, between 140,000 and 280,000, between 140,000 and 260,000, between 140,000 and 240,000, between 140,000 and 220,000, between 140,000 and 200,000, between 140,000 and 180,000, between 140,000 and 160,000, between 240,000 and 500,000, between 160,000 and 480,000, between 160,000 and 460,000, between 160,000 and 440,000, between 160,000 and 420,000, between 160,000 and 400,000, between 160,000 and 380,000, between 160,000 and 360,000, between 160,000 and 340,000, between 160,000 and 320,000, between 160,000 and 300,000, between 160,000 and 280,000, between 160,000 and 260,000, between 160,000 and 240,000, between 160,000 and 220,000, between 160,000 and 200,000, between 160,000 and 180,000, between 180,000 and 500,000, between 180,000 and 480,000, between 180,000 and 460,000, between 180,000 and 440,000, between 180,000 and 420,000, between 180,000 and 400,000, between 180,000 and 380,000, between 180,000 and 360,000, between 180,000 and 340,000, between 180,000 and 320,000, between 180,000 and 300,000, between 180,000 and 280,000, between 180,000 and 260,000, between 180,000 and 240,000, between 180,000 and 220,000, between 180,000 and 200,000, between 200,000 and 500,000, between 200,000 and 480,000, between 200,000 and 460,000, between 200,000 and 440,000, between 200,000 and 420,000, between 200,000 and 400,000, between 200,000 and 380,000, between 200,000 and 360,000, between 200,000 and 340,000, between 200,000 and 320,000, between 200,000 and 300,000, between 200,000 and 280,000, between 200,000 and 260,000, between 200,000 and 240,000, between 200,000 and 220,000, between 220,000 and 500,000, between 220,000 and 480,000, between 220,000 and 460,000, between 220,000 and 440,000, between 220,000 and 420,000, between 220,000 and 400,000, between 220,000 and 380,000, between 220,000 and 360,000, between 220,000 and 340,000, between 220,000 and 320,000, between 220,000 and 300,000, between 220,000 and 280,000, between 220,000 and 260,000, between 220,000 and 240,000, between 240,000 and 500,000, between 240,000 and 480,000, between 240,000 and 460,000, between 240,000 and 440,000, between 240,000 and 420,000, between 240,000 and 400,000, between 240,000 and 380,000, between 240,000 and 360,000, between 240,000 and 340,000, between 240,000 and 320,000, between 240,000 and 300,000, between 240,000 and 280,000, between 240,000 and 260,000, between 260,000 and 500,000, between 260,000 and 480,000, between 260,000 and 460,000, between 260,000 and 440,000, between 260,000 and 420,000, between 260,000 and 400,000, between 260,000 and 380,000, between 260,000 and 360,000, between 260,000 and 340,000, between 260,000 and 320,000, between 260,000 and 300,000, between 260,000 and 280,000, between 280,000 and 500,000, between 280,000 and 480,000, between 280,000 and 460,000, between 280,000 and 440,000, between 280,000 and 420,000, between 280,000 and 400,000, between 280,000 and 380,000, between 280,000 and 360,000, between 280,000 and 340,000, between 280,000 and 320,000, between 280,000 and 300,000, between 300,000 and 500,000, between 300,000 and 480,000, between 300,000 and 460,000, between 300,000 and 440,000, between 300,000 and 420,000, between 300,000 and 400,000, between 300,000 and 380,000, between 300,000 and 360,000, between 300,000 and 340,000, between 300,000 and 320,000, between 320,000 and 500,000, between 320,000 and 480,000, between 320,000 and 460,000, between 320,000 and 440,000, between 320,000 and 420,000, between 320,000 and 400,000, between 320,000 and 380,000, between 320,000 and 360,000, between 320,000 and 340,000, between 340,000 and 500,000, between 340,000 and 480,000, between 340,000 and 460,000, between 340,000 and 440,000, between 340,000 and 420,000, between 340,000 and 400,000, between 340,000 and 380,000, between 340,000 and 360,000, between 360,000 and 500,000, between 360,000 and 480,000, between 360,000 and 460,000, between 360,000 and 440,000, between 360,000 and 420,000, between 360,000 and 400,000, between 360,000 and 380,000, between 380,000 and 500,000, between 380,000 and 480,000, between 380,000 and 460,000, between 380,000 and 440,000, between 380,000 and 420,000, between 380,000 and 400,000, between 400,000 and 500,000, between 400,000 and 480,000, between 400,000 and 460,000, between 400,000 and 440,000, between 400,000 and 420,000, between 420,000 and 500,000, between 420,000 and 480,000, between 420,000 and 460,000, between 420,000 and 440,000, between 440,000 and 500,000, between 440,000 and 480,000, between 440,000 and 460,000, between 460,000 and 500,000, between 460,000 and 480,000, or between 480,000 and 500,000 human CD303 molecules per cell.

According to a preferred embodiment, the cell line according to the invention has on its surface between 20,000 and 60,000, preferably between 25,000 and 50,000, human CD303 molecules per cell. Indeed, such numbers of human CD303 molecules per cell make it possible to effectively and reproducibly discriminate antibodies against human CD303 antigen.

Dual Vector or Kit with Two Vectors

According to a second aspect, the invention consists of an expression vector comprising a first nucleic acid molecule encoding human CD303 antigen and a second nucleic acid molecule encoding the gamma chain of human FcεRI. Alternatively, the nucleic acid molecules encoding human CD303 antigen and the gamma chain of human FcεRI, respectively, are present on two independent expression vectors.

According to a third aspect, the present invention is a transfection kit comprising an expression vector comprising a first nucleic acid molecule encoding human CD303 antigen and a second nucleic acid molecule encoding the gamma chain of human FcεRI, or two expression vectors each comprising a nucleic acid molecule encoding human CD303 antigen and the gamma chain of human FcεRI, respectively.

Each vector according to the invention or included in a transfection kit according to the invention comprises the elements necessary for expression of said nucleic acid molecule, and notably a promoter, a transcription initiation codon, termination sequences, and suitable transcription regulatory sequences. These elements vary according to the host used for expression and are easily selected by a person skilled in the art based on their general knowledge. The vector may notably be a plasmid vector or a viral vector.

In the case of a mammalian cell line, a human cell line such as the Jurkat line, or a human pDC cell line such as CAL-1, any expression vector allowing expression in mammalian cells may be used.

Examples of such vectors include the vector pcDNA4/TO (Invitrogen) used to express the gamma chain of human FcεRI in a Jurkat E6-1 line (ATCC® TIB-152™, ECACC 88042803), or the vector pcDNA3.1(−) used in Example 1 to express human CD303 antigen.

Uses

According to a fourth aspect the invention relates to the use of the cell line according to the invention to characterize a functional activity of an antibody against human CD303 antigen, preferably an activity of the ADCC, CDC, cytokine secretion, apoptosis or phagocytosis type, or to compare the binding affinity of several anti-CD303 antibodies to human CD303 antigen or the epitopes of human CD303 antigen recognized by several anti-CD303 antibodies.

According to a fifth aspect, the invention relates to the use of the cell line according to the invention to characterize the functional capabilities (notably capabilities of the ADCC, CDC, cytokine secretion, apoptosis and phagocytosis type) of effector cells from a human subject, in particular a human subject suffering from BPDCN or an autoimmune disease.

Characterization of Anti-CD303 Antibodies

Anti-CD303 Antibodies that May be Characterized Using the Cells According to the Invention By "antibody" is meant a molecule comprising at least one binding domain for a given antigen and a constant domain comprising an Fc fragment capable of binding to Fc receptors (FcR). In most mammals, such as humans and mice, an antibody is composed of four polypeptide chains: two heavy chains and two light chains bound together by a variable number of disulfide bridges providing flexibility to the molecule. Each light chain consists of a constant domain (CL) and a variable domain (VL); the heavy chains consist of a variable domain (VH) and three or four constant domains (CH1 to CH3 or CH1 to CH4) according to the isotype of the antibody. The variable domains are involved in antigen recognition, while the constant domains are involved in the biological, pharmacokinetic and effector properties of the antibody.

The variable region differs from one antibody to another. Indeed, the genes encoding antibody heavy and light chains are respectively generated by recombination of three and two distinct gene segments called VH, DH and JH-CH for the heavy chain and VL and JL-CL for the light chain. The CH and CL segments do not take part in recombination and form the constant regions of the heavy and light chains, respectively. Recombinations of the VH-DH-JH and VL-JL segments form the variable regions of the heavy and light chains, respectively. The VH and VL regions each have three hypervariable zones or complementarity-determining regions (CDRs) called CDR1, CDR2 and CDR3, with CDR3 being the most variable since it is located in the recombination zone. These three CDRs, and particularly CDR3, are found in the portion of the antibody that comes in contact with the antigen and are thus very important for antigen recognition. Thus, antibodies retaining the three CDRs and each of the heavy and light chains of an antibody mostly retain the antigen specificity of the original antibody. In a certain number of cases, an antibody retaining only one of the CDRs, and notably CDR3, also retains the specificity of the original antibody. CDR1, CDR2 and CDR3 are each preceded by FR1, FR2 and FR3, respectively, corresponding to framework regions (FRs) that vary the least from one VH or VL segment to another. CDR3 is also followed by a framework region, FR4.

In the context of the invention, any antibody against human CD303 antigen may be characterized using the cells according to the invention, irrespective of the primary sequences of its heavy and light chains, and notably irrespective of the CDR1, CDR2 and CDR3 sequences of the heavy and light chains.

Unlike the variable domains, whose sequence strongly varies from one antibody to another, the constant domains are characterized by an amino acid sequence that is very similar from one antibody to another, typical of the species and the isotype, with optionally a few somatic mutations. The Fc fragment naturally consists of the heavy chain constant region excluding the CH1 domain, i.e., the lower hinge region and the constant domains CH2 and CH3 or CH2 to CH4 (depending on the isotype). In human IgG1, the complete Fc fragment consists of the C-terminal portion of the heavy chain starting from the cysteine residue at position 226 (C226), the numbering of amino acid residues in the Fc fragment being throughout the present description that of the EU index described in Edelman et al.—1969 and Kabat et al.—1991. The corresponding Fc fragments of other types of immunoglobulins may easily be identified by a person skilled in the art by sequence alignments.

The Fc fragment is glycosylated in the CH2 domain with the presence, on each of the two heavy chains, of an N-glycan bound to the asparagine residue at position 297 (Asn297). Glycosylation is known to influence the effector functions of the antibody, such as its ADCC and CDC activities. Notably, it is known today that the fucose content of an antibody composition plays a crucial role in the ability of said composition to induce a strong ADCC response via FcγRIII (WO01/77181, Shields et al.—2002; Shinkawa et al.—2003). The antibody to be characterized on the functional level in the context of the invention may have a low fucose content, notably of less than or equal to 65%. By "fucose content" is meant the percentage of fucosylated forms within N-glycans attached to the Asn297 residue of the Fc fragment of each heavy chain of each antibody. By "low fucose content" is meant a fucose content of less than or equal to 65%, or even lower, but not necessarily nil. The fucose content may for example be between 5% and 65%, between 5% and 50%, or between 10% and 50%. The antibody, functional fragment or derivative thereof according to the invention may moreover have different types of glycosylation (N-glycans of the oligomannose or biantennary complex type, with a variable proportion of bisecting N-acetylglucosamine (GlcNAc) residues, or of galactose residues in the case of N-glycans of the biantennary complex type), provided that they have a low fucose content. Antibodies having slightly fucosylated N-glycans were notably obtained by:

Production in YB2/0 (see EP1176195A1, WO01/77181, Shinkawa et al.—2003), CHO Lec13 (see Shields et al.—2002), EB66® (Olivier et al.—2010), the rat hepatoma cell lines H4-II-E (DSM ACC3129), H4-II-Es (DSM ACC3130) (see WO2012/041768) and the human lines NM-H9D8 (DSM ACC2806), NM-H9D8-E6 (DSM ACC 2807) and NM H9D8-E6Q12 (DSM ACC 2856) (see WO2008/028686).

Production in a wild-type CHO cell line in the presence of small interfering RNAs against FUT8 (Mori et al.—2004, Suzuki et al.—2007, Cardarelli et al.—2009, Cardarelli et al.—2010, Herbst et al.—2010) or GMD (gene encoding the GDP-fucose transporter in the Golgi apparatus, see Imai-Nishiya et al.—2007).

Production in a CHO cell line in which both alleles of the FUT8 gene encoding 1,6-fucosyltransferase have been deleted (Yamane-Ohnuki et al.—2004), or in which both alleles of the GMD gene encoding the GDP-fucose transporter in the Golgi apparatus have been deleted (Kanda et al.—2007).

Production in a CHO cell line in which the gene encoding the GnTIII (β(1,4)-N-acetylglucosaminetransferase III) enzyme was overexpressed transgenically (Umana et al.—1999). In addition to low fucosylation, the N-glycans obtained are characterized by a high bisecting GlcNAc content.

Production in transgenic plants (N. benthamiana), with a strong reduction of the β1,2-xylose and α1,3-fucose residue contents by the use of small interfering RNAs (Forthal et al.—2010).

In addition to, or alternatively to, a low fucose content, the antibody to be characterized on the functional level in the context of the invention may have a high galactose content. By "galactose content" or "degree of galactosylation" of the antibody is meant a percentage calculated from an analytical chromatogram of the N-glycans released from the antibody, according to the following formula:

$$\text{galactose content} = \frac{\sum_{i=1}^{n} (\text{number of } Gal) \times (\% \text{ relative area})}{\sum_{i=1}^{n} (\text{number of } A) \times (\% \text{ relative area})} \times 100$$

wherein:
"n" is the number of N-glycan peaks analyzed on a chromatogram, for example a normal-phase high-performance liquid chromatography (NP-HPLC) spectrum,
"number of Gal" is the number of galactoses on the antenna of the glycan corresponding to the peak,
"number of A" is the number of N-acetyl-glucosamine antennas of the glycan form corresponding to the peak, and
"% relative area" is the percentage of the area under the corresponding peak.

By "high galactose content" is meant a galactose content of greater than or equal to 30%.

The following binding domains, located in the Fc, are important for the biological properties of the antibody:
the neonatal Fc receptor (FcRn) binding domain, involved in the pharmacokinetic properties (in vivo half-life) of the antibody:
Different data suggest that certain residues located at the interface of the CH2 and CH3 domains are involved in FcRn binding.
the complement C1q protein binding domain, involved in the complement-dependent cytotoxicity (CDC) response: located in the CH2 domain;
the Fc receptor (FcR) binding domain, involved in responses of the phagocytosis or antibody-dependent cell cytotoxicity (ADCC) type: located in the CH2 domain.

Within the meaning of the invention, the Fc fragment of an antibody may be natural, as defined above, or else may have been modified in various ways, provided that it comprises a functional FcR (FcγR for IgG) binding domain, and preferably a functional FcRn binding domain. The modifications may include deletion of certain portions of the Fc fragment, provided that the latter contains a functional FcR (FcγR for IgG) binding domain, and preferably a functional FcRn binding domain. The modifications may further include various amino acid substitutions able to affect the biological properties of the antibody, provided that the latter contains a functional FcR binding domain, and preferably a functional FcRn binding domain. In particular, when the antibody is an IgG, it may comprise mutations intended to increase FcγRIIIa (CD16a)-binding, as described in WO00/42072, Shields et al.—2001, Lazar et al.—2006, WO2004/029207, WO2004/063351, WO2004/074455. Mutations for increasing FcRn binding and thus in vivo half-life may also be present, as described for example in Shields et al.—2001, Dall'Acqua et al.—2002, Hinton et al.—2004, Dall'Acqua et al. —2006(a), WO00/42072, WO02/060919, WO2010/045193, or WO2010/106180. Other mutations, such as those for decreasing or increasing binding to complement proteins and thus the CDC response, may optionally be present (see WO99/51642, WO2004/074455, Idusogie et al.—2001, Dall'Acqua et al.—2006(b), and Moore et al.—2010).

In the context of the invention, the antibodies to be characterized may be antibodies from any type of animal (notably murine, chimeric, humanized or human antibodies). Notably, for characterization of affinity for the antigen, any type of antibody (murine or other animal, chimeric, humanized or human) can be used. For characterization of a functional activity, the antibody to be characterized is preferably a chimeric, humanized or human antibody, thus making it possible to test the antibody's functions in a human context (human effector cells, human serum, etc.).

By "chimeric" antibody is meant an antibody that contains a natural variable region (light chain and heavy chain) derived from an antibody of a given species in combination with the light and heavy chain constant regions of an antibody of a species heterologous to said given species. Advantageously, if the monoclonal antibody composition for use as a medicinal product according to the invention comprises a chimeric monoclonal antibody, the latter comprises human constant regions. From a non-human antibody, a chimeric antibody can be prepared by using the genetic recombination techniques well-known to a person skilled in the art. For example, the chimeric antibody can be prepared by cloning the heavy and light chains of a recombinant DNA comprising a promoter and a sequence encoding the variable region of the non-human antibody, and a sequence encoding the constant region of a human antibody. For methods for preparing chimeric antibodies, reference may be made, for example, to the document by Verhoeyen et al.—1988.

By "humanized" antibody is meant an antibody that contains CDRs derived from an antibody of non-human origin, the other portions of the antibody molecule being derived from one (or several) human antibodies. Moreover, certain residues of the framework regions (FRs) may be modified to retain binding affinity (Jones et al.—1986; Verhoeyen et al. 1988; Riechmann et al.—1988). The humanized antibodies according to the invention can be prepared by techniques known to a person skilled in the art, such as CDR grafting, resurfacing, superhumanization, human string content, FR libraries, guided selection, FR shuffling and humaneering technologies, as summarized in the review by Almagro et al.—2008.

In the context of the invention, the antibodies to be characterized are advantageously monoclonal antibodies. By "monoclonal antibody" or "monoclonal antibody composition" is meant a composition comprising antibody molecules having an identical and unique antigen specificity. The antibody molecules present in the composition are likely to vary in terms of their post-translational modifications, and notably in terms of their glycosylation structures or their isoelectric point, but have all been encoded by the same heavy and light chain sequences and thus have, before any post-translational modification, the same protein sequence. Certain differences in protein sequences, related to post-translational modifications (such as for example cleavage of the heavy chain C-terminal lysine, deamidation of asparagine residues and/or isomerization of aspartate residues), may nevertheless exist between the various antibody molecules present in the composition.

In the context of the invention, the antibodies to be characterized may be of several isotypes. Indeed, the antibodies may be of several isotypes, according to the nature of their constant region: the γ, α, μ, ε and δ constant regions correspond to immunoglobulins IgG, IgA, IgM, IgE and IgD, respectively. Advantageously, the monoclonal antibody present in a composition used as a medicinal product in the context of the invention is of isotype IgG. Indeed, this isotype shows an ability to generate antibody-dependent cell cytotoxicity (ADCC) activity in the greatest number of individuals (humans). The γ constant regions comprise several subtypes: γ1, γ2, γ3, these three types of constant regions having the feature of binding human complement, and γ4, thus creating the subtypes IgG1, IgG2, IgG3, and IgG4. Advantageously, the monoclonal antibody to be characterized on the functional level in the context of the invention is of isotype IgG1 or IgG3, preferably IgG1.

The antibody to be characterized on the functional level in the context of the invention may be produced from any suitable host cell, transgenic non-human animal, or transgenic plant. The antibodies against human CD303 antigen expressed by the cell line according to the invention which are to be characterized may be intended for the treatment or prevention of hematopoietic tumors expressing CD303 antigen. These are notably blastic plasmacytoid dendritic cell neoplasms (BPDCN) of phenotype CD4+, CD11c−, Lin−, CD303+, CD304+, CD56+. These antibodies may also be intended for the treatment or prevention of inflammatory diseases, notably autoimmune diseases, diseases involving pDCs, and more particularly diseases involving IFN-α secretion by pDCs, such as atopic dermatitis, contact dermatitis, psoriasis, systemic lupus erythematosus, dermatomyositis, Sjögren's syndrome, type 1 b diabetes, autoimmune thrombocytopenia (or thrombopenia) (notably idiopathic thrombocytopenic purpura, or ITP), systemic scleroderma (also called progressive systemic scleroderma or systemic sclerosis), rheumatoid arthritis.

In the context of the present invention, the cell lines according to the invention thus make it possible to evaluate the functional activity of an antibody against human CD303 antigen or to compare the affinity of several anti-CD303 antibodies for human CD303 antigen or the epitopes of human CD303 antigen recognized by several anti-CD303 antibodies.

Characterization of ADCC Activity

In a first embodiment, the use of the cell lines according to the invention is directed at characterizing the ADCC activity of anti-human CD303 antibody. Thus, the invention relates to the use of the cell line according to the invention to characterize the ADCC activity of an antibody against human CD303 antigen.

By "ADCC activity" (ADCC being the abbreviation for "antibody-dependent cell cytotoxicity") is meant the antibody's ability to induce death of target cells (here, cells of the cell line according to the invention) in the presence of effector cells of the immune system, by binding to target cells by means of its variable regions binding to the antigen located on the surface of the target cells, and by binding to effector cells by means of its Fc fragment binding to an Fc receptor (FcR; FcγR for IgG) located on the surface of effector cells.

The measurement of ADCC activity of an antibody is performed by conventional techniques. Notably, in an embodiment, the invention relates to a method for testing the ADCC activity of an antibody against human CD303 antigen, comprising the following steps:
  a) contacting the cell line according to the invention with an antibody against human CD303 antigen and effector cells;
  b) incubating for a suitable time to allow lysis of the cells of the cell line according to the invention of step a); and
  c) measuring the degree of lysis of the cells of the cell line according to the invention of step a).

In step a), the cell line according to the invention (target cells) is contacted with an antibody against human CD303 antigen to be characterized (as described above) and effector cells.

In the context of the characterization of ADCC activity, the effector cells must be capable of inducing lysis of the target cells. They may be monocytes, macrophages, T lymphocytes or NK cells. All these cells are present in peripheral blood mononuclear cells (PBMC), and PBMC may thus be used. The effector cells used are compatible with the antibodies to be characterized, and are thus from the same species as the Fc fragment of human anti-CD303 antibody to be characterized.

In the case of IgG, ADCC via FcγRIIIa is known to be essential for good activity in vivo, and the ADCC test according to the invention thus advantageously specifically measures ADCC via FcγRIIIa. The effector cells express for the most part two FcγR capable of inducing an ADCC response: the receptor with high affinity for the Fc fragment of IgG, FcγRI, and the receptor with low affinity for the Fc fragment of IgG, FcγRIIIa. NK cells are an exception and express only FcγRIIIa. Thus, for specifically measuring ADCC via FcγRIIIa, it is possible to use purified NK cells as effector cells. Alternatively, it is also possible to use effector cells expressing both FcγRI and FcγRIIIa (or a mixture of cells, some expressing both FcγRI and FcγRIIIa and others only FcγRIIIa) and to saturate the FcγRI having high affinity for the Fc fragment of IgG by adding to the reaction medium polyvalent IgG, i.e., polyclonal IgG with multiple antigenic specificities, purified from plasma. When human effector cells are used, one may notably use IVIG, or normal human immunoglobulins, or polyvalent IgG, a medicinal product used in the treatment of certain autoimmune diseases.

The target cells (cells expressing on their surface human CD303 antigen recognized by the antibody to be tested, here cells of the cell line according to the invention) may have been labeled intracellularly beforehand with a marker making it possible in step c) to measure the number of target cells actually lysed. Any suitable marker, such as a radioactive, fluorescent, luminescent or chromogenic marker, can be used. Alternatively, the target cells may not be labeled beforehand. In this case, assay of a protein present in the target cells (such as the LDH enzyme present in all cell types) can be used to measure the number of cells lysed in step c).

Target cells (cells expressing on their surface human CD303 antigen recognized by the antibody to be tested, here cells of the cell line according to the invention) and effector cells are present in an effector/target (E:T) ratio close to physiological conditions in vivo.

An ADCC dose-response curve is generally constructed. To this end, increasing amounts of antibody are contacted with target cells and effector cells in separate wells and ADCC is measured at various concentrations of antibody. Each point is generally evaluated multiple times (notably in duplicate or triplicate).

Negative controls are also prepared, generally:
  spontaneous lysis or release (SR), obtained by contacting target cells with only antibodies (without effector cells),
  natural cytotoxicity (NC) of effector cells, obtained by contacting target cells with only effector cells (without antibody).

A positive control of maximum lysis, obtained by lysing target cells with a chemical, may also be used.

In step b), incubation (generally at 37° C.) is carried out for a suitable time to allow lysis of the target cells (cells of the cell line according to the invention). The duration of the incubation may vary between a few hours and about a day, notably between 1 and 24 hours, in particular 4 to 24 hours. A person skilled in the art can determine an optimal time according to the particular test conditions.

Finally, in step c), the degree of lysis of the target cells (cells of the cell line according to the invention) is measured. This is generally carried out by centrifuging the plates used for contacting and incubation, by collecting the supernatant and by measuring either the amount of intracellular marker of the target cells labeled beforehand released into the medium, or the amount or the activity of a protein initially present in the target cells and released into the medium following lysis of the target cells.

If the above-mentioned controls are used, the percentage of lysis can then be calculated according to one of the following formulae:

$$\% \text{ lysis}=[(ER-SR)/(100-SR)]-[(NC-SR)/(100-SR)]$$

or $$\% \text{ lysis}=ER-NC-SR$$

Where SR and NC are as defined above, and ER corresponds to the lysis obtained for the test sample.

The results (% lysis) are expressed as a function of antibody dilution factor. For each antibody, a "50% activity" or "EC50" value may be calculated, which corresponds to the antibody dilution factor necessary to induce 50% of the plateau value obtained for this antibody.

A precise example of the test for ADCC via FcγRIIIa according to the invention is as follows: Fc γ-chain-CD303 Jurkat cells (35,000 cells/well) or CAL-1 cells stably transfected with an expression vector comprising a nucleic acid molecule encoding human CD303 antigen are incubated in a 96-well flat-bottom plate with NK cells and increasing concentrations of anti-CD303 antibody for 4 hours at 37° C. After incubation, the supernatant is collected. Lysis of the target cells induced by the anti-CD303 antibodies is measured chromogenically by quantifying the intracellular lactate dehydrogenase (LDH) enzyme released into the supernatant by the lysed target cells (Cytotoxicity Detection Kit (LDH), Roche Diagnostics).

The percentage of lysis is calculated according to the following formula:

$$\% \text{ lysis}=[(ER-SR)/(100-SR)]-[(NC-SR)/(100-SR)]$$

where ER and SR represent the experimental release (ER) and the spontaneous release (SR) of LDH, respectively, and NC represents the natural cytotoxicity of the NK cells.

The results (% lysis) are expressed as a function of antibody dilution factor. For each antibody, the "50% activity" value corresponds to the antibody dilution factor necessary to induce 50% of the plateau value obtained for this antibody. This value can be calculated with the PRISM software.

Characterization of Cytokine Secretion-Inducing Activity

In another embodiment, the use of the cell lines according to the invention is directed at characterizing the cytokine secretion-inducing activity of human anti-CD303 antibody. Thus, the invention relates to the use of the cell line according to any one of claims 1 to 6 to characterize the cytokine secretion-inducing activity of an antibody against human CD303 antigen.

By "cytokine secretion-inducing activity" is meant the antibody's ability to induce the secretion of various cytokines by effector cells of the immune system.

The measurement of the cytokine secretion-inducing activity of an antibody is performed by conventional techniques. Notably, in an embodiment, the invention relates to a method for testing the cytokine secretion-inducing activity of an antibody against human CD303 antigen, comprising the following steps:
  a) contacting the cell line according to the invention with an antibody against human CD303 antigen and effector cells;
  b) incubating for a suitable time to allow the effector cells to secrete at least one cytokine; and
  c) measuring the secretion rate of at least one cytokine.

In step a), the cell line according to the invention (target cells) is contacted with an antibody against human CD303 antigen to be characterized (as described above) and effector cells. The effector cells that can be used and the contacting conditions are same as those for the characterization of ADCC (see above).

In step b), incubation (generally at 37° C.) is carried out for a suitable time to allow the effector cells to secrete at least one cytokine. The incubation time can vary between a few hours and about a day, notably between 1 and 24 hours, in particular 4 to 24 hours. A person skilled in the art can determine an optimal time according to the particular test conditions. Finally, in step c), the secretion rate of at least one cytokine is measured, by conventional technologies well-known to a person skilled in the art, such as flow cytometry assay of culture supernatants. The cytokines tested may notably include IL-2, IL-10, IFN-γ and TNF-α.

Characterization of Complement-Dependent Cytotoxicity (CDC) Activity

In another embodiment, the use of the cell lines according to the invention is directed at characterizing the CDC activity of human anti-CD303 antibody. Thus, the invention relates to the use of the cell line according to any one of claims 1 to 6 to characterize the CDC activity of an antibody against human CD303 antigen.

By "CDC activity" (CDC being the abbreviation for "complement-dependent cytotoxicity") is meant the antibody's ability to induce death of target cells (here, cells of the cell line according to the invention) in the presence of complement proteins, by binding to target cells by means of its variable portions binding to the antigen located on the surface of the target cells, on the one hand and by binding to complement proteins, on the other hand.

The measurement of the CDC activity of an antibody is performed by conventional techniques. Notably, in an embodiment, the invention relates to a method for testing the CDC activity of an antibody against human CD303 antigen, comprising the following steps:
  a) contacting the cell line according to the invention with an antibody against human CD303 antigen and a source of complement proteins;
  b) incubating for a suitable time to allow lysis of the cells of the cell line according to the invention of step a); and
  c) measuring the degree of lysis of the cells of the cell line according to the invention of step a).

In step a), the cell line according to the invention (target cells) is contacted with an antibody against human CD303 antigen to be characterized (as described above) and a source of complement proteins, generally serum.

Here again, the target cells (cells expressing on their surface human CD303 antigen recognized by the antibody to be tested, here cells of the cell line according to the invention) may have been labeled intracellularly beforehand with a marker making it possible in step c) to measure the number of target cells actually lysed. Any suitable marker, such as a radioactive, fluorescent, luminescent or chromogenic marker, can be used. Alternatively, the target cells may not be labeled beforehand. In this case, assay of a protein present in the target cells (such as the LDH enzyme present in all cell types) can be used to measure the number of cells lysed in step c).

Here again, an ADCC dose-response curve is generally constructed. To this end, increasing amounts of antibody are contacted with target cells and effector cells in separate wells and ADCC is measured at various concentrations of antibody. Each point is generally evaluated multiple times (notably in duplicate or triplicate).

Here again, controls are generally carried out to estimate in step c) the percentage of lysis obtained at each concentration of antibody tested. To this end, one prepares a calibration range obtained with various dilutions of target cells lysed with a chemical such as a detergent (2% Triton X-100, for example) respectively corresponding to various percentages of lysis (for example 100%, 50%, 25% and 0% lysis). The controls also include spontaneous release (target cells alone).

In step b), incubation (generally at 37° C.) is carried out for a suitable time to allow lysis of the target cells (cells of the cell line according to the invention). The incubation time can vary between a few hours and about a day, notably between 1 and 24 hours, in particular 1 to 2 hours. A person skilled in the art can determine an optimal time according to the particular test conditions.

Finally, in step c), the degree of lysis of the target cells (cells of the cell line according to the invention) is measured. The results are calculated according to the following formula:

% lysis=(% lysis with antibody and complement)−(% lysis with antibody without complement).

A precise example of the CDC test according to the invention is as follows:

Fc γ-chain-CD303 Jurkat cells or CAL-1 cells stably transfected with an expression vector comprising a nucleic acid molecule encoding human CD303 antigen are incubated with increasing concentrations of anti-CD303 antibody (0 to 5,000 ng/mL) and in the presence of baby rabbit serum as source of (1:10 dilution).

After 2 h of incubation at 37° C., the amount of intracellular lactate dehydrogenase (LDH) enzyme released into the supernatant by the lysed target cells is measured with the Cytotoxicity Detection Kit (LDH) (Roche Diagnostics, item no. 11644793001).

Characterization of Antibody-Induced Apoptosis

In another embodiment, the use of the cell lines according to the invention is directed at characterizing the apoptotic activity of human anti-CD303 antibody. Thus, the invention relates to the use of the cell line according to any one of claims 1 to 6 to characterize the apoptosis-inducing activity of an antibody against human CD303 antigen.

By "apoptotic activity" is meant the ability of the antibody to be characterized to induce apoptosis in cells expressing the antigen recognized by the antibody.

The measurement of the apoptotic activity of an antibody is performed by conventional techniques, such as conventional flow-cytometry tests for apoptosis using propidium iodide and annexin V. Notably, in an embodiment, the invention relates to a method for testing the apoptotic activity of an antibody against human CD303 antigen, comprising the following steps:
 a) contacting the cell line according to the invention with an antibody against human CD303 antigen;
 b) incubating for a suitable time to allow the antibody to induce apoptosis in the cells of the cell line according to the invention of step a); and
 c) measuring the percentage of apoptotic cells of the cell line according to the invention of step a).

In step a), the cell line according to the invention (target cells) is contacted with an antibody against human CD303 antigen to be characterized (as described above), in the presence or absence of a crosslinker (antibody or antibody fragment against the Fc fragment, for example).

In step b), incubation (generally at 37° C.) is carried out for a suitable time to allow lysis of the target cells (cells of the cell line according to the invention). The incubation time can vary between a few hours and about a day, notably between 1 and 24 hours, and in particular is 16 hours. A person skilled in the art can determine an optimal time according to the particular test conditions.

Finally, in step c), the percentage of apoptotic cells is measured. This measurement can be performed by flow cytometry, by labeling the cells with propidium iodide (P1) and annexin V.

The combination of these two labels makes it possible to differentiate living cells (annexin V and PI negative) from cells in the early phase of apoptosis (annexin V positive, PI negative) or in the late phase of apoptosis (annexin V positive, PI positive).

A precise example of the apoptotic activity test according to the invention is as follows: Target cells (cells of a cell line according to the invention, $2.5 \cdot 10^5$) are incubated with the anti-CD303 antibody to be characterized (1 μg/mL) with or without crosslinker (for example goat anti-human IgG Fcγ F(ab')$_2$ at 10 μg/mL) in 1 mL of RPMI 10% FCS, in P24 plates for 24 hours at 37° C. The cells are then centrifuged, washed twice in PBS, taken up in the buffer provided by the kit and incubated with annexin V-FITC and propidium iodide (PI) according to the recommendations of BD Biosciences. The cells are analyzed with the flow cytometer; the percentage of apoptotic cells corresponds to the cells labeled with annexin V (annexin V and annexin V+PI).

Characterization of Phagocytosis Activity

In another embodiment, the use of the cell lines according to the invention is directed at characterizing the phagocytosis activity of human anti-CD303 antibody. Thus, the invention relates to the use of the cell line according to any one of claims 1 to 6 to characterize the phagocytosis-inducing activity of an antibody against human CD303 antigen.

By "phagocytosis activity" is meant the antibody's ability to induce phagocytosis of target cells expressing the antigen recognized by the antibody by effector cells of the immune system able to phagocytose (monocytes, macrophages, neutrophils and dendritic cells), by binding to target cells by means of its variable portions binding to the antigen located on the surface of the target cells, and by binding to effector cells by means of its Fc fragment binding to an Fc receptor (FcR; FcγRI, FcγRIIA, FcγRIIB2 for IgG) located on the surface of the effector cells.

The measurement of the ADCC activity of an antibody is performed by conventional techniques. Notably, in an embodiment, the invention relates to a method for testing the ADCC activity of an antibody against human CD303 antigen, comprising the following steps:
 a) contacting the cell line according to the invention with an antibody against human CD303 antigen and effector cells able to phagocytose;
 b) incubating for a suitable time to allow phagocytosis of the cells of the cell line according to the invention of step a); and
 c) measuring the rate of phagocytosis of the cells of the cell line according to the invention of step a).

In step a), the cell line according to the invention (target cells) is contacted with an antibody against human CD303 antigen to be characterized (as described above) and effector cells able to phagocytose. In the context of the characterization of phagocytosis activity, the effector cells must be able to phagocytose. They may be monocytes, macrophages or neutrophils.

In the case of IgG, phagocytosis occurs via one of the receptors FcγRI, FcγRIIA and FcγRIIB2 present on the surface of the effector cells able to phagocytose. FcγRI having high affinity, unlike FcγRIIA and FcγRIIB2, phagocytosis activity via FcγRIIA and FcγRIIB2 can be measured using polyvalent IgG as described above for ADCC.

The target cells (cells expressing on their surface human CD303 antigen recognized by the antibody to be tested, here cells of the cell line according to the invention) may have been labeled intracellularly beforehand with a marker making it possible in step c) to measure the number of target cells actually phagocytosed. Any suitable marker, such as a radioactive, fluorescent, luminescent or chromogenic marker, can be used.

Target cells (cells expressing on their surface human CD303 antigen recognized by the antibody to be tested, here cells of the cell line according to the invention) and effector cells are present in an effector/target (E:T) ratio close to physiological conditions in vivo.

A phagocytosis activity dose-response curve is generally constructed. To this end, increasing amounts of antibody are contacted with target cells and effector cells in separate wells and phagocytosis activity is measured at various concentrations of antibody. Each point is generally evaluated multiple times (notably in duplicate or triplicate).

A positive control is also prepared: natural phagocytosis (NP), obtained by contacting the target cells with only effector cells (without antibody).

In step b), incubation (generally at 37° C.) is carried out for a suitable time to allow phagocytosis of the target cells (cells of the cell line according to the invention). The incubation time can vary between a few hours and about a day, notably between 1 and 24 hours, in particular 4 to 24 hours. A person skilled in the art can determine an optimal time according to the particular test conditions.

Finally, in step c), the rate of phagocytosis of the target cells (cells of the cell line according to the invention) is measured. This is generally performed by removing the non-phagocyted target cells by washing (the effector cells able to phagocytose generally being adherent) and by measuring the number of target cells labeled beforehand present in the phagocytes.

The percentage of phagocytosis or index of phagocytosis can then be calculated according to the following formula:

% phagocytosis=(% of effector cells containing at least one target cell)×(average number of target cells per effector cell containing target cells).

The results (% phagocytosis) are expressed as a function of antibody dilution factor. For each antibody, a "50% activity" or "EC50" value can be calculated, which corresponds to the antibody dilution factor necessary to induce 50% of the plateau value obtained for this antibody.

Comparison of the Affinity of Several Anti-CD303 Antibodies for Human CD303 Antigen In another embodiment, the invention relates to the use of the cell line according to the invention to compare the binding affinity of several anti-CD303 antibodies to human CD303 antigen.

The binding affinity of an anti-CD303 antibody to human CD303 antigen can be measured by using a cell line according to the invention by any technology known to a person skilled in the art.

Notably, the binding of the anti-CD303 antibodies to be tested to the human CD303 expressed by the cell line according to the invention can be studied by flow cytometry. To this end, cells of the cell line according to the invention are first incubated for 30 minutes at 4° C. with an antibody (anti-CD303 or negative control) at various concentrations (0-40 µg/mL, final concentration). After washing with the diluent, the antibodies are visualized by adding a phycoerythrin (PE)-coupled goat anti-mouse IgG F(ab')$_2$ fragment (100 µL diluted to 1:100 in the diluent) for 45 minutes at 4° C. The cells are then washed and analyzed by flow cytometry (FC500, Beckman Coulter).

The results are expressed as a dose-response curve, with concentration on the x axis and mean fluorescence intensity (MFI) on the y axis.

The values at the plateau (Bmax, mean maximum fluorescence intensity) can be estimated after modeling the curves, for example using the GraphPad PRISM® software, and compared between the various anti-CD303 antibodies to be tested. A value denoted EC50, representing the amount of antibody necessary to reach 50% of the Bmax value, can also be calculated. The EC50 values of the various antibodies to be tested can be compared.

Comparison of the Epitopes of Human CD303 Antigen Recognized by Two Anti-CD303 Antibodies In another embodiment, the invention relates to the use of the cell line according to the invention to compare the epitopes of human CD303 antigen recognized by several anti-CD303 antibodies.

In order to compare the epitopes of human CD303 antigen recognized by two anti-CD303 antibodies, the antibodies to be tested can be placed in competition for binding to a cell line according to the invention with various anti-CD303 antibodies whose epitope is known. Notably, one of the two antibodies to be tested is preferably carrying a detection marker and is contacted with a cell line according to the invention in the absence or in the presence of increasing concentrations of the other unlabeled anti-CD303 antibody. The labeling intensity of cells of the cell line according to the invention is then measured. If the epitopes recognized by the two antibodies are identical or overlap, competition between the two antibodies for binding to the cell line according to the invention is observed, i.e., the labeling intensity of cells of the cell line according to the invention decreases when the concentration of unlabeled antibody increases.

If the epitope of human CD303 antigen recognized by one of the two anti-CD303 antibodies is known, it may be possible to characterize the epitope recognized by the other anti-CD303 antibody.

Characterization of the Functional Capabilities of Effector Cells from a Human Subject The cell line according to the invention may also be used to characterize the functional capabilities (notably capabilities of the ADCC, CDC, cytokine secretion, apoptosis and phagocytosis type) of effector cells from a human subject, in particular a human subject suffering from BPDCN or an autoimmune disease.

Functional Capabilities to be Characterized

The functional capabilities that can be characterized are the same as above, notably capabilities of the ADCC, CDC, cytokine secretion, apoptosis and phagocytosis type.

The test methods are the same as described above for the characterization of anti-CD303 antibodies, except for the fact that the same antibody is used and that the controls used are control effector cells whose functional capabilities are known.

Effector Cells to be Characterized

The effector cells to be characterized can notably have been obtained beforehand from human subjects suffering from BPDCN or an autoimmune disease.

Effector cells from peripheral blood can be used for characterization, in the form of PBMC, or of purified effector cells, such as monocytes, macrophages, T lymphocytes or NK cells.

Kits for Characterizing Anti-CD303 Antibodies

According to a sixth aspect, the invention consists of a kit for characterizing anti-CD303 antibodies comprising the cell line according to the invention, and advantageously at least one reagent selected from effector cells, polyvalent IgG, and reference anti-CD303 antibodies.

EXAMPLES

Example 1. Preparation and Characterization of a Jurkat Cell Line Stably Expressing Human CD303 and the Gamma Chain of Human FcεRI Materials and Methods
Cells and Culture Conditions The Fc γ-chain Jurkat cell line (Jurkat Clone E6-1 line (ATCC® TIB-152™) stably transfected with an expression vector (pcDNA4/TO) for the gamma chain of human FcεRI) was cultured in RPMI 1640 medium with glutamine supplemented with 10% fetal calf serum (FCS) at 37° C. under 7% $CO_2$ in the air. The cells were seeded at $0.5 \cdot 10^5$ cells/mL three days before Nucleofection®.
Construction of the Vector The full-length cDNA encoding human CD303 antigen (GenBank/EMBL/DDBL, AF293615.1) was subcloned into the vector pcDNA3.1(−) (see map of this vector in FIG. 1).

After adding the BamHI and HindIII restriction sites, the Kozak sequence, and a second STOP codon, the coding sequence is synthesized by MWG.

The pcDNA3.1 vector was sequenced by MWG with the primer BGHpAPERC6-3' before starting the study in order to determine if the vector is (+) or (−), as the cloning sites are different in these two vectors. Sequencing showed that the vector is pcDNA3.1(−).

The CD303 coding sequence and the primers CD303-5' and CD303-3' are synthesized by MWG. Double digestion with BamHI and HindIII is performed on the MWG vector comprising the CD303 coding sequence and the vector pcDNA3.1(−). The digestion is confirmed on gel and the sequences are purified with NucleoSpin Extract II. CD303 is inserted into the vector pcDNA3.1(−) by ligation, then transformed into *E. coli*. PCR screening of seven bacterial colonies using the sense primer CD303-5': 5'-ACAT-TCACTGTCATGTACCTCAGAAGTC-3'; and the antisense primer BGHpAPERC6-3': 5'-CATGCCTGCTATT-GTCTTCCCA-3'. The PCR program used comprises 30 cycles notably consisting of hybridization (52° C.), elongation (30 seconds at 72° C.) and denaturation (95° C.) steps. Six colonies out of seven contain the CD303 insert (295-bp PCR product). From these six colonies four stock glycerols are prepared, and four bacterial cultures are purified in order to recover the pcDNA3.1(−) vector carrying the CD303 insert. A control digestion with BamHI and HindIII enzymes is performed in order to ensure the presence of the CD303 insert.

The sequence of the CD303 inserts present on pcDNA3.1(−) vectors purified by miniprep is confirmed by sequencing using the primers CD303-5' and CD303-3' (5'-AGACCT-TCAACTGGAACCACCAGAG-3').

The vectors are then purified by EndoFree Maxiprep and confirmed by sequencing with primers CD303-5' and CD303-3'.

The vectors are then linearized with ScaI and precipitated before being taken up in 1 μg/mL TE buffer.
Transfection of Fc γ-Chain Jurkat Cells Transfections were performed according to the procedures established for the Amaxa transfection systems (Amaxa Biosystems, Cologne, Germany). For nucleofection, $2 \cdot 10^6$ cells and 3 μg of linearized CD303 pcDNA3.1(−) vector were suspended in 100 μL of Nucleofector solution (Nucleofector™ Kit for Jurkat, Amaxa) according to the X-001 program. As control, 1 μg of enhanced green fluorescent protein (EGFP) plasmid DNA (pmaxGFP, Amaxa) was used with the same nucleofection protocol.

After transfection, the cells were spread on 6-well plates without antibiotic with culture medium. The selective medium was partly refreshed (about a half-volume) twice per week with an interval of 3-4 days.

After 24 h, the cells transfected with pmaxGFP were collected for measurements. Transfection efficiency was determined by FACS after transfection of pMax-GFP (Lonza, Allendale, N.J., USA).

After 48 h of culture, the transfected cells were analyzed by flow cytometry and the cells expressing CD303 on their surface were purified by fluorescence-activated cell sorting (FACS).
Fluorescence-Activated Cell Sorting Briefly, the pool of transfected cells were labeled with PE-labeled anti-CD303 antibodies (Miltenyi Biotec). Mouse monoclonal antibodies of the same PE (phycoerythrin) isotype were used as controls. The fluorescence-labeled cells were analyzed on an EPICS ALTRA fluorescence-activated cell sorter (Beckman).

Geneticin selection was started 24 hours after cell sorting, by application of 1 mg/mL of G418 (Sigma) to the culture medium.
Limiting-Dilution Cloning The cells were then seeded at $1 \cdot 10^5$ cells/mL for 48 hours before cloning. The day of cloning, the cells were counted; viability must be greater than 80% to continue. The cells were resuspended in RPMI+10% FCS (2 cells/mL) and were seeded on 96-well plates (200 μL/well corresponding to 0.4 cell/well). The cells were incubated at 37° C., 7% $CO_2$ for 10 to 12 days. The medium was partly refreshed (about a half-volume) twice per week with an interval of 3-4 days.
Determination of the Number of CD303 Molecules Per Cell The determination of the number of CD303 molecules per cell of one of the Fc γ-chain-CD303 Jurkat clones is performed by flow cytometry, using the QIFIKIT (Dako), and murine anti-CD303 antibody AC144.

Cells of one of the Fc γ-chain-CD303 Jurkat clones and the antibodies are prepared in diluent (PBS+1% FCS).

$1 \cdot 10^5$ cells are incubated at 4° C. for 30 minutes with 100 μL of antibody (anti-CD303 or negative control) at various concentrations (0-40 μg/mL, final concentration).

After washing with the diluent, the antibodies are visualized by adding a phycoerythrin (PE)-coupled goat anti-mouse IgG F(ab')$_2$ fragment (100 μL diluted to 1:100 in the diluent) for 45 minutes at 4° C. The cells are then washed and analyzed by flow cytometry (FC500, Beckman Coulter).
Results
FACS Selection of Fc γ-Chain Jurkat Cells Transfected with CD303

Figure 2:
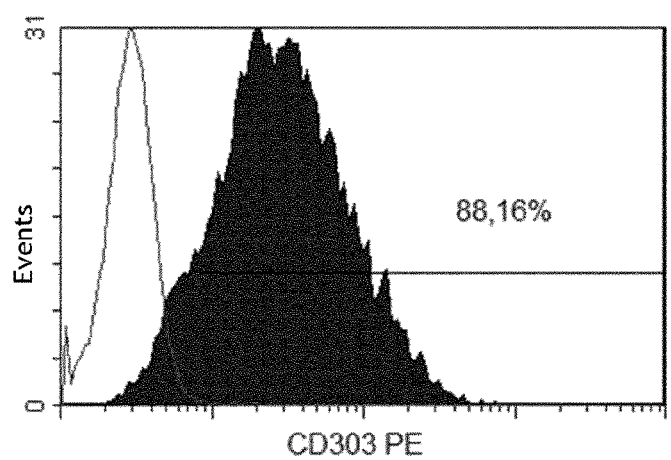
FIG. 2. CD303 expression on cells of pool 008-1 at day 43. The histograms show cells labeled with PE-conjugated anti-CD303 antibody (filled region) and with PE-conjugated control isotype antibody (line).

Before cell sorting, nearly 0.4% of the cells expressed CD303 (data not shown). CD303-positive cells were isolated by FACS (20,767 cells, pool 008-2) and were seeded in RPMI medium+10% FCS. Unfortunately, these cells do not grow in these culture conditions. CD303-negative cells were seeded under geneticin selection (day 3). At day 25, 35% of these cells expressed CD303. After a second cell sorting, almost 73% of the cells were positive for CD303; and after 18 more days under geneticin selection, more than 88% of the cells expressed CD303 (FIG. 2).

Figure 3:
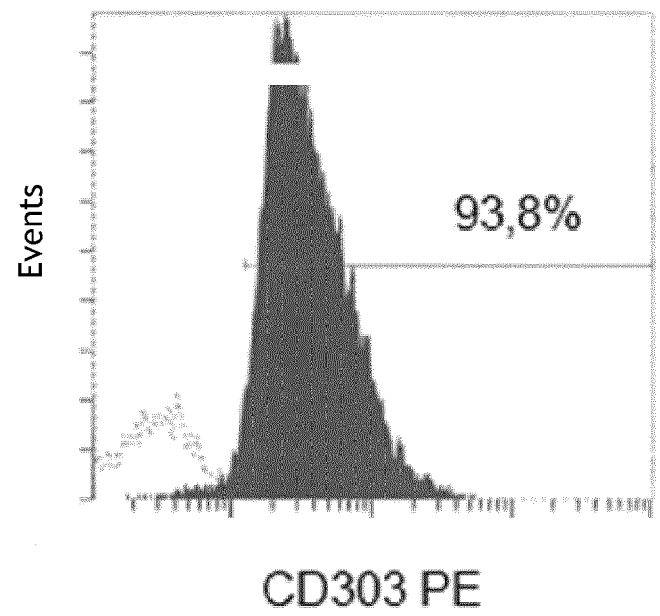
FIG. 3. CD303 expression on cells of pool 008-1 after the third cell sorting. The histograms show cells stained with PE-conjugated anti-CD303 antibody (filled region) and with PE-conjugated control isotype antibody (dotted line).
Figure 4:
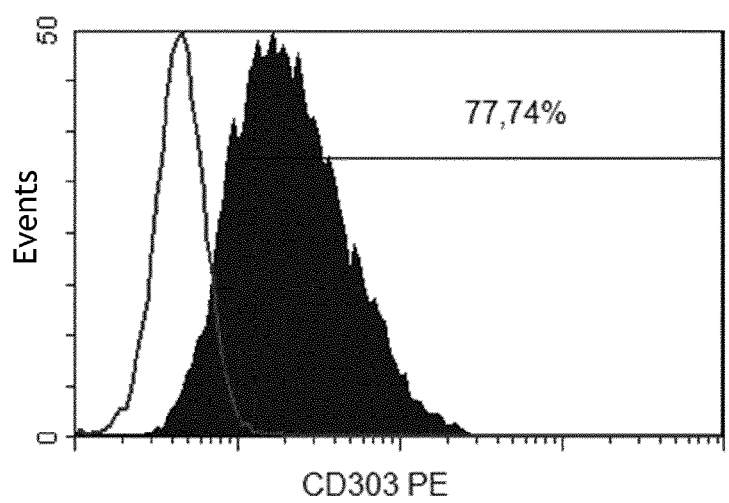
FIG. 4. CD303 expression on cells of pool 008-1 after the third cell sorting and 2 months of culture. The histograms show cells stained with PE-conjugated anti-CD303 antibody (filled region) and with PE-conjugated control isotype antibody (line).

At day 44, after a third cell sorting, almost 93% of the cells expressed CD303 (FIG. 3). Stability of CD303 expression: after two months of culture under geneticin selection, more than 77% of the cells still expressed CD303 (FIG. 4).

Limiting-Dilution Cloning of CD303+ Cells

Moreover, we performed limiting-dilution cloning of the stable Fc γ-chain Jurkat transfectants expressing CD303.

Figure 5:
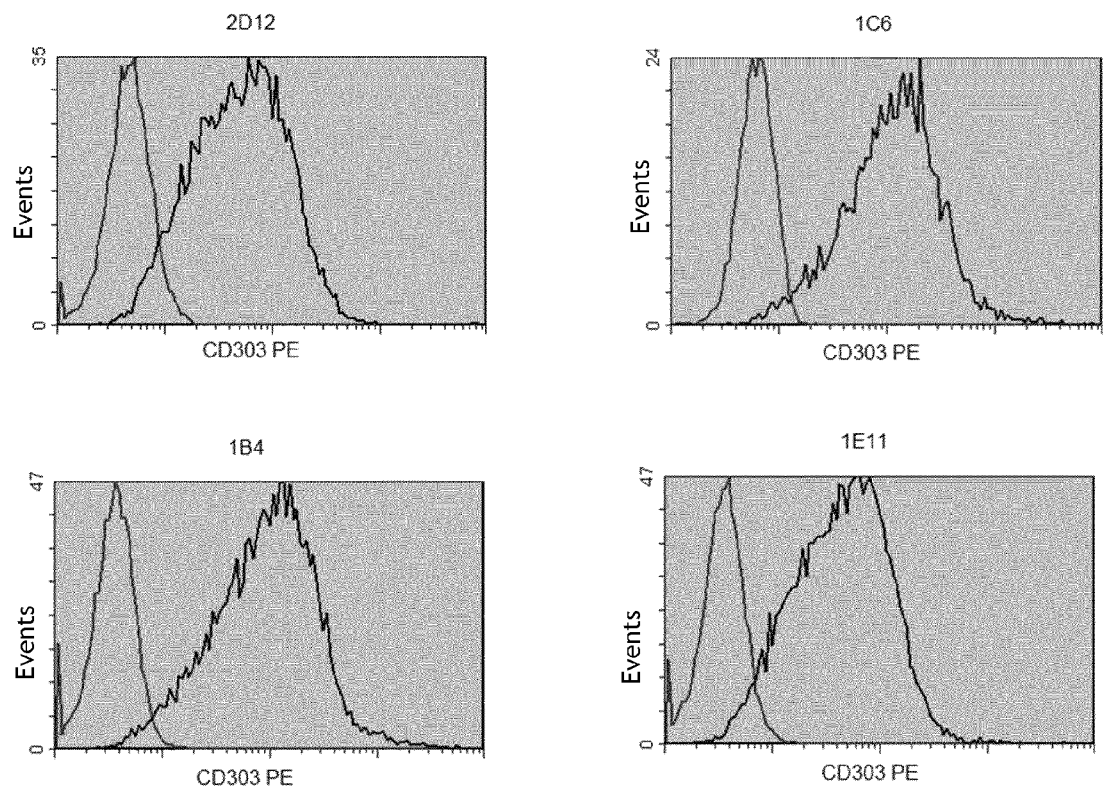
FIG. 5. CD303 expression by clones obtained after limiting-dilution cloning. The histograms show cells labeled with PE-conjugated anti-CD303 antibody (at right) and with PE-conjugated control isotype antibody (at left).

Twenty-seven clones were isolated and tested by staining with anti CD303-PE antibody. Only four clones were selected and thawed; more than 80% of the cells expressed CD303 (FIG. 5).

Determination of the Number of CD303 Molecules Per Cell

One of the clones was then characterized in terms of the number of CD303 molecules per cell. The results show the number of CD303 molecules per cell to be 28,325±5,405.

Conclusion

After transfection with a CD303 pcDNA3.1(−) vector, geneticin selection, and fluorescence-activated cell sorting, a stable pool of Fc γ-chain CD303+ Jurkat cells (more than 80% positive cells) is now available and represents a useful tool for in vitro characterization of anti-CD303 antibodies.

Example 2. Transfection of pDCs for Overexpression of CD303

Transfection of CAL-1 cells (pDCs) to overexpress CD303 is performed with the Amaxa Human Dendritic Cell Nucleofector Kit.

The day before transfection, the cells are inoculated at $2 \cdot 10^5$ cells/mL. The day of transfection, the CAL-1 cells have a cell density of $4.6 \cdot 10^5$ cells/mL and 85% viability.

The day of transfection:
EMS medium+10% FCS (fetal calf serum) is prewarmed at 37° C. for 1 hour (1 F25 flask containing 7.5 mL and 2 wells of a P6 plate containing 1.5 mL),
the "supplement" available in the kit (135 μL) is added to the "Nucleofector" solution (615 μL).
$7 \cdot 10^6$ cells are centrifuged at 200 g for 10 minutes ($1 \cdot 10^6$ cells/cuvette).
The pellet is then taken up in 700 μL of Nucleofector solution and distributed at 100 μL per Eppendorf tube.
3 μL (3 μg) of CD303 pcDNA3.1(−) vector, and 4 μL (2 μg) of pmax-GFP vector or no vector (pilot negative), are added per Eppendorf tube.
The cell suspension is transferred to cuvettes and the U-002 program is applied.
500 μL of prewarmed medium is added to the cuvette and the cell suspension is gently transferred to a F25 flask or a P6 plate containing medium as follows:
5 cuvettes comprising CD303 pcDNA3.1(−) are taken up in 10 mL of medium in an F25 flask;
1 cuvette comprising Pmax-GFP is taken up in 2 mL of medium on a P6 plate;
1 cuvette comprising T- is taken up in 2 mL of medium on a P6 plate.
The cuvettes are then incubated at 37° C. with $CO_2$.

Figure 6:
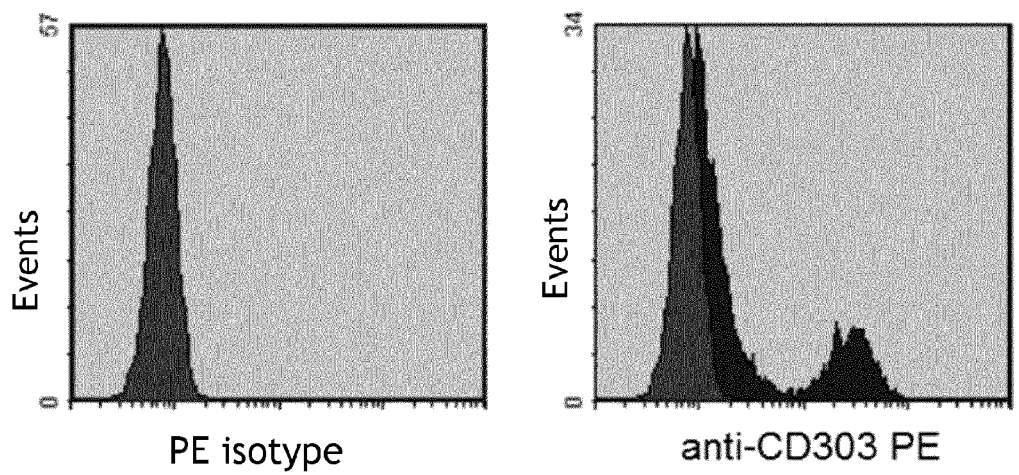
FIG. 6. Labeling of the pool of CAL-1 cells transfected with a CD303 expression vector with a PE control isotype antibody or an anti-CD303-PE antibody at day 22 after transfection.

From Day 1 to Day 51:
At day 1: Measurements of GFP by cytometry and by fluorescence microscopy are performed to estimate transfection efficiency. Measurements by cytometry reveal 49% transfected cells and by microscopy 43% transfected cells.
At day 3: The cells are counted and the pellet is taken up at $5 \cdot 10^5$ cells/mL in selection medium (EMS+10% FCS+1 g/L G418).
At day 6: The cells are counted and the pellet is taken up at $4 \cdot 10^5$ cells/mL in selection medium (EMS+10% FCS+1 g/L G418).
CD303-transfected CAL-1: $8.1 \cdot 10^5$/mL cells and 49% viability.
Negative control CAL-1: $2.6 \cdot 10^5$ cells/mL and 42.6% viability.
At day 8: The cells are counted and a portion of the cells are transferred to a P24 plate (1 mL/well) and the remainder to an F150 flask (56 mL).
CD303-transfected CAL-1: $0.22 \cdot 10^5$ cells/mL and 3% viability.
Negative control CAL-1: $0.1 \cdot 10^5$ cells/mL and 1.5% viability.
At day 10: The CD303-transfected CAL-1 cells are counted.
F150: $0.08 \cdot 10^5$ cells/mL and 1.3% viability. The cells are centrifuged and the pellet is taken up in 65 mL so as not to exceed $5 \cdot 10^5$ dead cells/mL.
P24: Half of the medium is changed.
Negative control: $0.0 \cdot 10^5$ cells/mL and 0% viability→Stop.
At day 13: The CD303-transfected CAL-1 cells are counted.
F150: $0.04 \cdot 10^5$ cells/mL and 0.7% viability. The cells are centrifuged and the pellet is taken up in 70 mL so as not to exceed $5 \cdot 10^5$ dead cells/mL.
P24: Half of the medium is changed.
At day 17: The CD303-transfected CAL-1 cells are counted.
F150: $0.04 \cdot 10^5$ cells/mL and 1.0% viability. The cells are centrifuged and the pellet is taken up in 56 mL so as not to exceed $5 \cdot 10^5$ dead cells/mL.
P24: Half of the medium is changed.
At day 20: The CD303-transfected CAL-1 cells are counted.
F150: $0.002 \cdot 10^5$ cells/mL and 0.5% viability.→Stop.
P24: one well is counted: $16.4 \cdot 10^5$ cell/mL and 53.8% viability.
P24 transferred to 3 F75 flasks (8 P24 wells per F75 in 30 mL final).
At day 22: The CD303-transfected CAL-1 cells are counted.
F75: $12.8 \cdot 10^5$ cells/mL and 85% viability.
The pool is labeled with anti-CD303-PE. Only a small proportion of the cell population expresses CD303 at a high level (see FIG. 6).
Eight cryotubes are frozen in liquid nitrogen.
Reinoculation at $3 \cdot 10^5$ cells/mL in an F75 flask.
At day 24: The CD303-transfected CAL-1 cells are counted.
F75: $19.9 \cdot 10^5$ cells/mL and 95% viability. Reinoculation at $2 \cdot 10^5$ cells/mL in an F75 flask.
Cloning at 40 cells/P96 in EMS+10% FCS+0.5 g/L G418 and preparation of 5 cloning plates.
From day 28 to day 37: The CD303-transfected CAL-1 cells are counted.
F75: Reinoculation at $2 \cdot 10^5$ cells/mL in an F75 flask 3 times per week.
Cloning: Half of the medium is changed once per week.
From day 38 to day 50: The CD303-transfected CAL-1 cells are counted.
F75: Reinoculation at $2 \cdot 10^5$ cells/mL in an F75 flask 3 times per week.
Cloning: The clones are transferred to a P24 plate and then to a P6 plate for screening CD303 expression by cytometry.

Figure 7:
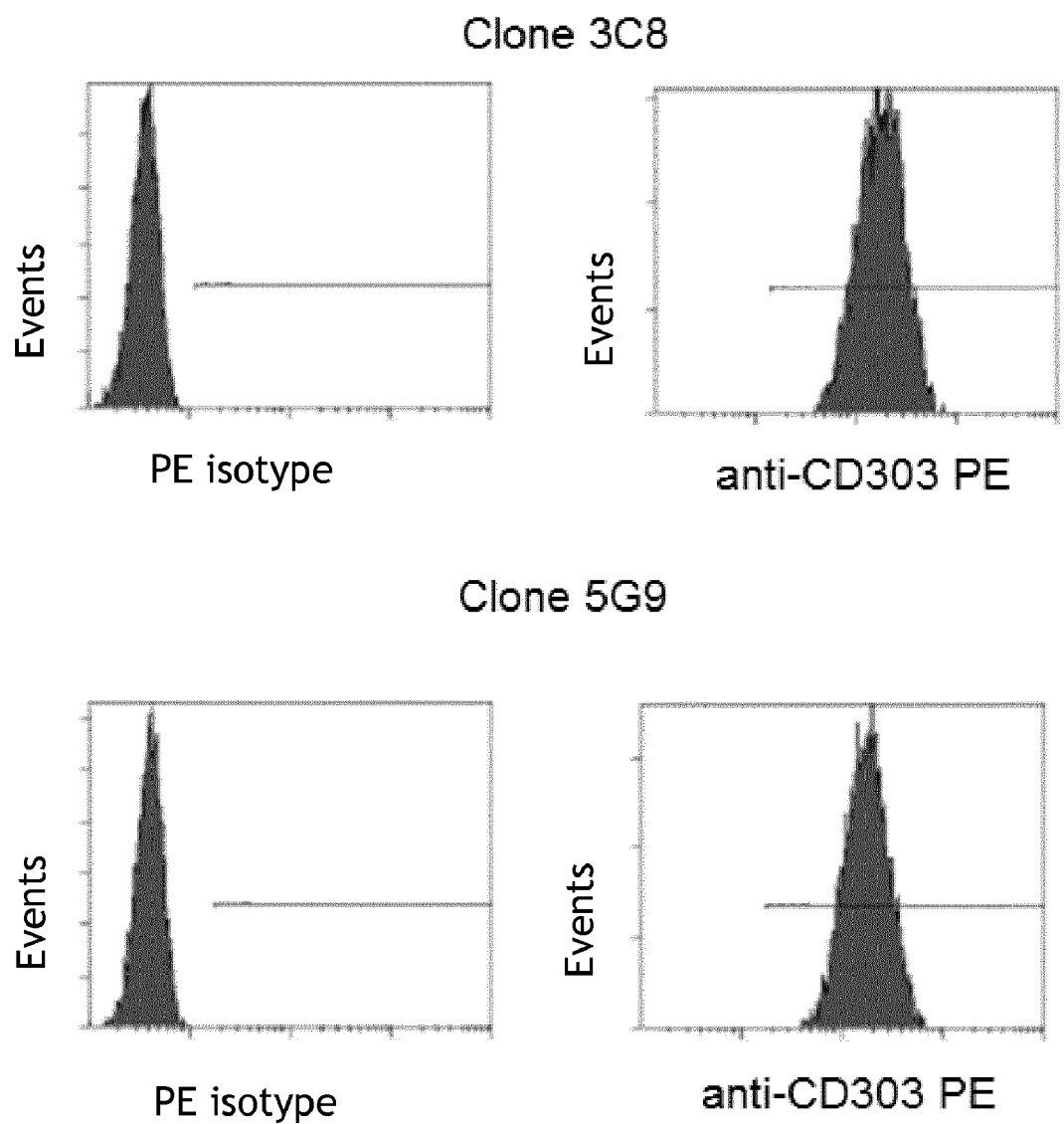
FIG. 7. Labeling of clones NF-3C8 and NF-5G9 obtained after cloning at day 50 after transfection with a PE control isotype antibody or an anti-CD303-PE antibody.

Thirty clones are screened and 2 positive clones, NF-3C8 and NF-5G9, are retained (see FIG. 7).

At day 51: Eight cryotubes of clones NF-3C8 and NF-5G9 are frozen and the clones in culture are maintained at $0.5 \cdot 10^5$ cells/mL; reinoculation twice per week.

The CAL-1 cells and the two clones, NF-3C8 and NF-5G9, were then characterized in terms of the number of CD303 molecules per cell, by flow cytometry, using the QIFIKIT (Dako), and murine anti-CD303 antibody AC144, according to the protocol described in Example 1.

The results show the number of CD303 molecules per cell to be 3,000-6,000 (or about 4,500 on average) for the CAL-1 cells and from 40,000 to 50,000 (or about 45,000 on average) CD303 molecules per cell for the two clones. The two clones, NF-3C8 and NF-5G9, thus have high surface expression of CD303 compared to the original CAL-1 cell line, with an amplification factor of about 10 (or an increase of about 900% relative to the original CAL-1 cell line).

Example 3. Three-Month Stability Study of Clones NF-3C8 and NF-5G9 in the Presence and Absence of G418

Materials and Methods

The cells are reinoculated twice per week at $0.5 \cdot 10^5$ cells/mL in an F25 flask (10 mL) in EMS medium+10% FCS+0.5 g/L G418.

CD303 expression is evaluated every 2 weeks by cytometry.

Labeling is performed on ice using anti-CD303-PE (AC144) (Miltenyi Biotec, item no. 130-090-511) diluted to 1:10 in PBS+1% FCS.

Results

Figure 8:
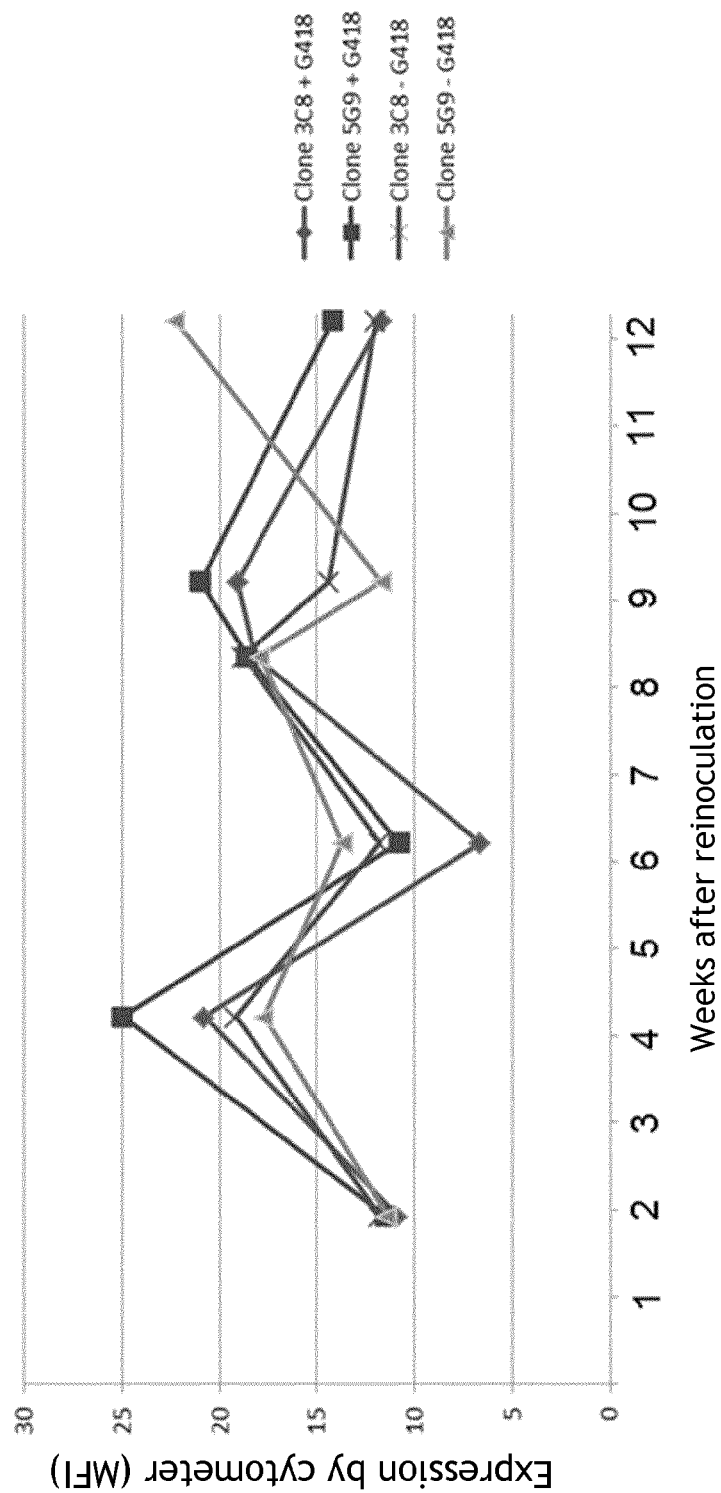
FIG. 8. Stability of the high CD303 expression by clones NF-3C8 and NF-5G9 obtained by transfection of CAL-1 cells with a CD303 expression vector. Evolution of PE anti-CD303 antibody labeling of clones NF-3C8 and NF-5G9 between 2 and 12 weeks after reinoculation in the presence or absence of G418.
Figure 9A:
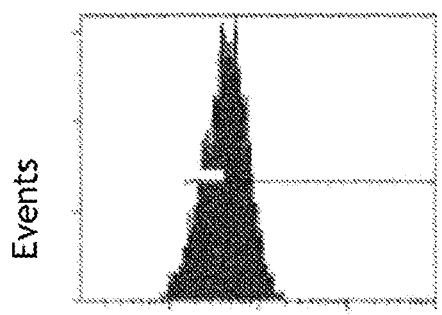
FIG. 9. Stability of the high CD303 expression by clones NF-3C8 and NF-5G9 obtained by transfection of CAL-1 cells with a CD303 expression vector. PE anti-CD303 antibody labeling of clones NF-3C8 (A) and NF-5G9 (B) at 2 and 12 weeks after reinoculation in the presence or absence of G418.
Figure 9A:
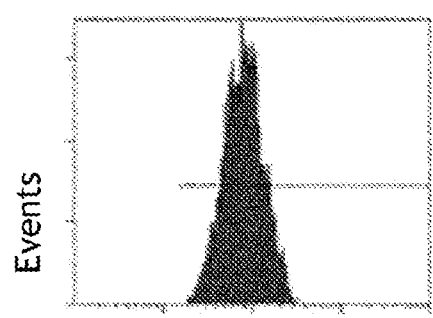
Figure 9A:
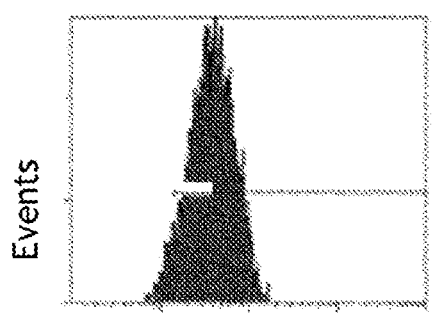
Figure 9A:
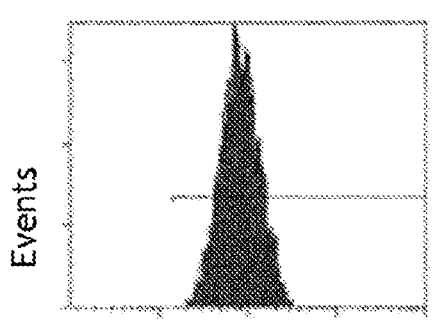
Figure 9B:
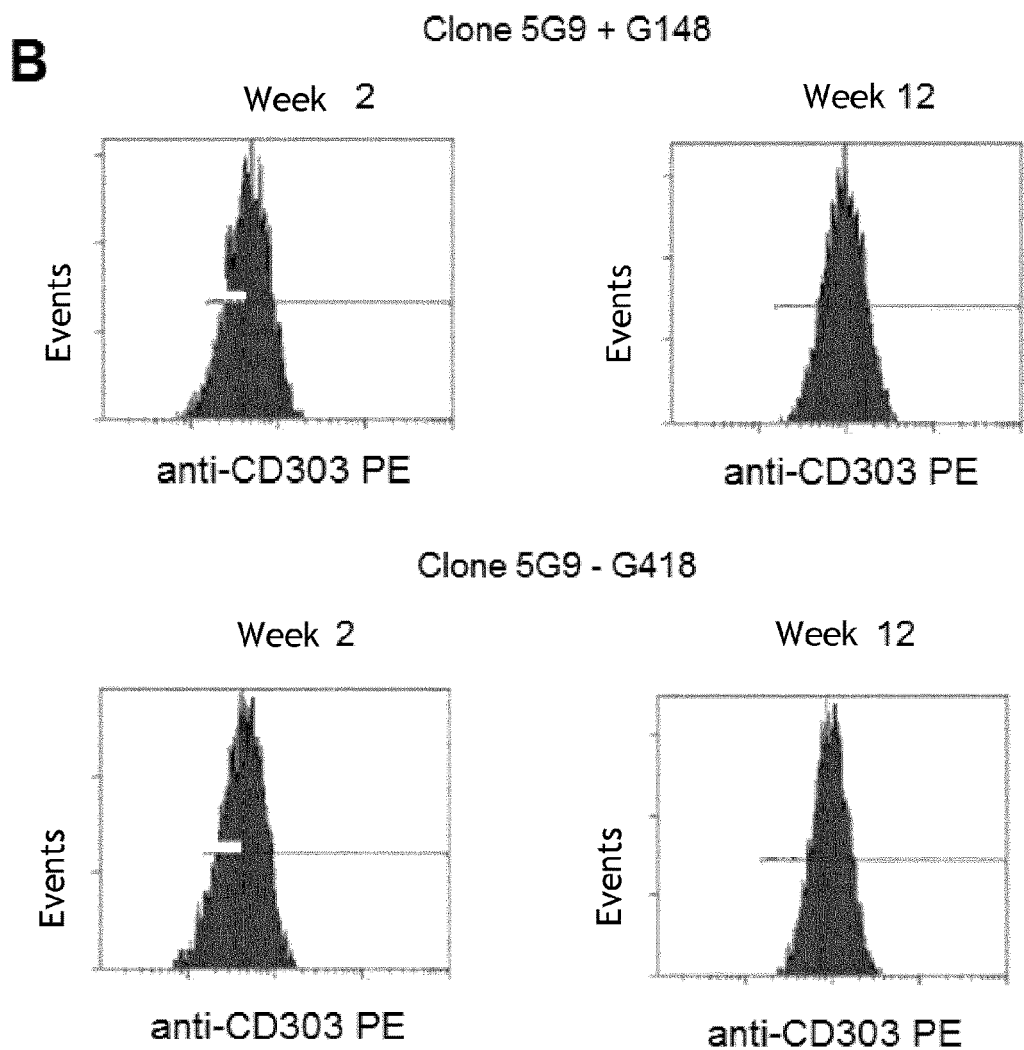

The results of labeling by cytometry are presented in FIGS. 8 and 9.

The MFI values are slightly variable according to the tests but no loss of CD303 expression is observed after 12 weeks of culture in the absence of G418. CD303 expression is thus stable for the two clones tested.

Example 4. Characterization of Chimeric Anti-CD303 Antibodies Using CD303-Jurkat Cells or Clones NF-3C8 and NF-5G9

Materials and Methods

Antibodies

Five chimeric anti-(human CD303) antibodies were tested, named 122A2, 102E9, 114D11, 104C12 and 104E10. A control antibody against another antigen and a humanized anti-(human CD303) antibody called BIIB059 were also used.

CD303-Binding Test

Fc γ-chain-CD303 Jurkat cells or NF-3C8 and NF-5G9 cells, on the one hand, and antibodies, on the other, are prepared in diluent (PBS+1% FCS).

$1 \cdot 10^5$ cells are incubated at 4° C. for 30 minutes with 100 μL of antibody (anti-CD303 or negative control) at various concentrations (0-40 μg/mL, final concentration).

After washing with the diluent, the antibodies are visualized by adding a phycoerythrin (PE)-coupled goat anti-mouse IgG F(ab')2 fragment (100 μL diluted to 1:100 in the diluent) for 45 minutes at 4° C. The cells are then washed and analyzed by flow cytometry (FC500, Beckman Coulter).

Test for ADCC Via CD16a

Fc γ-chain-CD303 Jurkat cells (35,000 cells/well) are incubated in a 96-well flat-bottom plate with NK cells and increasing concentrations of anti-CD303 antibody for 4 hours at 37° C. After incubation, the supernatant is collected. Lysis of the target cells induced by the anti-CD303 antibodies is measured chromogenically by quantifying the intracellular lactate dehydrogenase (LDH) enzyme released into the supernatant by the lysed target cells (Cytotoxicity Detection Kit (LDH), Roche Diagnostics).

The percentage of lysis is calculated according to the following formula:

$$\% \text{ lysis} = [(ER-SR)/(100-SR)] - [(NC-SR)/(100-SR)]$$

where ER and SR represent the experimental release (ER) and the spontaneous release (SR) of LDH, respectively, and NC represents the natural cytotoxicity of the NK cells. The results (% lysis) are expressed as a function of antibody dilution factor. For each antibody, the "50% activity" value corresponds to the antibody dilution factor necessary to induce 50% of the plateau value obtained for this antibody. This value was calculated with the PRISM software.

Results

CD303-Binding Test

Figure 10:
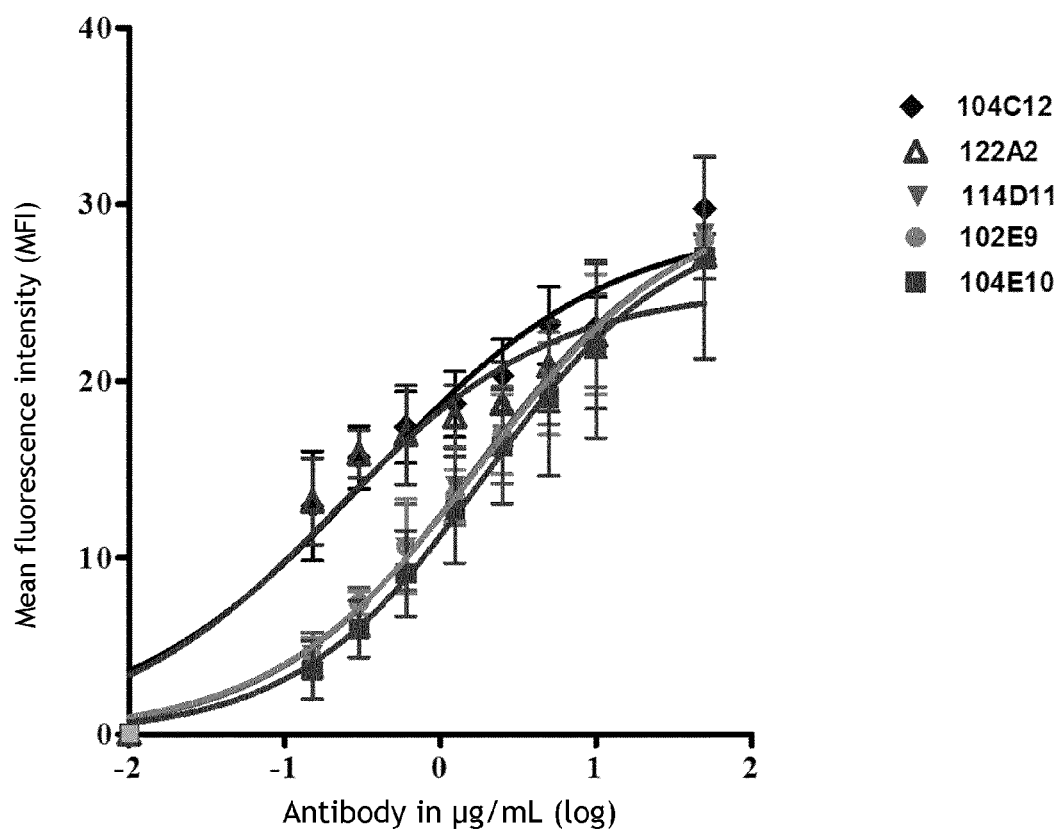
FIG. 10. Binding of the antibodies to human CD303 antigen expressed on NF-3C8 or NF-5G9.

The results are presented in FIG. 10, and show that it is possible to distinguish differences in binding to human CD303 antigen by using clone NF-3C8 or alternatively NF-5G9.

ADCC Test

ADCC activity via CD16a obtained with the chimeric anti-CD303 antibodies 122A2 and 114D1 or with a control antibody, in the presence of the CAL-1 line not transfected with an expression vector for human CD303 antigen, is represented in FIG. 11A. The low specific ADCC activity (about 10%) observed with the CAL-1 cell line is likely due to a low number of CD303 sites (between 3,000 and 6,000 sites).

ADCC activity via CD16a obtained with the chimeric anti-CD303 antibodies 122A2 and ch.102E9, with the humanized anti-CD303 antibody BIIB059, or with a control antibody, in the presence of the CAL-1 line transfected with an expression vector for human CD303 antigen expressing 40,000 to 50,000 human CD303 antigen molecules on its surface (clone NF-3C8), is represented in FIG. 11B and in Table 1 below.

TABLE 1

ADCC activity via CD16a obtained with the chimeric anti-CD303 antibodies 122A2 and ch.102E9, with the humanized anti-CD303 antibody BIIB059, or with a control antibody.

|  | Control | ch.122A2 | ch.102E9 | BIIB059 |
|---|---|---|---|---|
| Emax (% lysis) | n/a | 39.94 | 40.19 | 29.30 |
| EC50 (ng/mL) | n/a | 0.04 | 0.05 | 1.68 |

Emax: maximum % lysis obtained at the plateau with high concentration of antibody.
EC50: concentration of antibody to obtain 50% of the maximum lysis.

Clearly, clone NF-3C8 makes it possible, much better than the untransfected CAL-1 line, to detect the ADCC response via CD16a induced by the various anti-CD303 antibodies.

The ADCC activity via CD16a induced by the chimeric anti-CD303 antibodies 122A2 and 114D1 is about 40 times higher than that induced by the humanized anti-CD303 antibody BIIB059.

CONCLUSIONS

The data presented above clearly show the usefulness of the lines according to the invention for characterizing and discriminating anti-CD303 antibodies for therapeutic use.

REFERENCES

Almagro et al. Frontiers in Bioscience 13, 1619-1633, Jan. 1, 2008.
Cardarelli et al. Cancer Immunol Immunother. 2010. 59. 257-265,
Cardarelli et al. Clin Cancer Res 2009 Apr. 28; 15:3376-3383.
Dall'Acqua et al. 2002, J Immunol.; 169:5171-80.
Dall'Acqua et al. 2006, J. Biol. Chem.; 281:23514-24. (a).
Dall'Acqua et al. *J Immunol* 2006; 177:1129-1138. (b).
Edelman, G. M. et al., Proc. Natl. Acad. USA, 63, 78-85 (1969).
EP1176195A1
Forthal et al., *J Immunol* 2010; 185; 6876-6882.
Herbst R. et al. J Pharmacol Exp Ther. 2010 October; 335(1):213-22.
Hinton et al. 2004, J Biol Chem.; 279:6213-6.
Idusogie E E et al. J Immunol. 2001; 166:2571-5.
Imai-Nishiya et al., BMC Biotechnology 2007, 7:84.
Jones et al. Nature, 321:522-525, 1986.
JP 5011520
Kabat et al., Sequences of Proteins of Immunological Interest, 5th Ed. Public Health Service, National Institutes of Health, Bethesda, Md. (1991).
Kanda Y et al., Journal of Biotechnology 130 (2007) 300-310.
Lazar, G. A., et al. Proc Natl Acad Sci USA. 103(11):4005-10.
Maeda T et al., Int J Hematol. 2005 February; 81(2):148-54
Moore G L. Et al. mAbs 2:2, 181-189; March/April, 2010.
Mori K, et al. Biotechnol Bioeng. 2004 Dec. 30; 88(7):901-8.
Olivier S. et al. MAbs. 2010 July-August; 2(4):405-415.
Riechmann et al. Nature, 332:323-327, 1988.
Shields R L, et al. J Biol Chem. 2001 Mar. 2; 276(9):6591-604.
Shields R L, et al. J Biol Chem. 2002 Jul. 26; 277(30):26733-40.
Shinkawa T, et al. J Biol Chem. 2003 Jan. 31; 278(5):3466-73.
Suzuki et al. Clin Cancer Res 2007 Mar. 15; 13:1875-1882.
Umana et al. Nat Biotechnol. 1999 February; 17(2):176-80.
Verhoeyen et al. Science, 239:1534-1536, 1988.
WO00/42072,
WO00/42072,
WO01/77181
WO02/060919,
WO2004/029207,
WO2004/063351,
WO2004/074455,
WO2008/028686
WO2010/045193,
WO2010/106180
WO2012/041768
WO2012/080642,
WO99/51642,
Yamane-Ohnuki N. et al. Biotechnol Bioeng. 2004 Sep. 5; 87(5):614-22.

---

The invention claimed is:

1. A cell line expressing the gamma chain of Fcε receptor I (FcεRI) and human CD303 antigen, wherein said cell line is stably transfected with an expression vector comprising a nucleic acid molecule encoding human CD303 antigen and has high expression of human CD303 on its surface, wherein said cell line has at least 10,000 human CD303 molecules per cell and said cell line is:
   a) a cell line of human plasmacytoid dendritic cells (pDCs) stably transfected with an expression vector comprising a nucleic acid molecule encoding human CD303 antigen; or
   b) a human lymphocyte cell line, stably transfected with an expression vector comprising a first nucleic acid molecule encoding human CD303 antigen and a second nucleic acid molecule encoding the gamma chain of human FcεRI, or with two expression vectors each comprising a nucleic acid molecule encoding human CD303 antigen and the gamma chain of human FcεRI, respectively.

2. The cell line according to claim 1, wherein said cell line is a cell line stably transfected with a vector comprising a nucleic acid molecule encoding human CD303 antigen, selected from the CAL-1 line or a human pDC line obtained from blastic plasmacytoid dendritic cell neoplasm (BPDCN) cells from a human patient by a method comprising the following steps:
   obtaining primary malignant BPDCN cells from peripheral blood of a patient diagnosed with BPDCN according to WHO classification; and
   cloning surviving cells after long-term culture to obtain a long-lasting cell line in culture.

3. The cell line according to claim 1, wherein said cell line is a Jurkat cell line, stably transfected with an expression vector comprising a first nucleic acid molecule encoding human CD303 antigen and a second nucleic acid molecule encoding the gamma chain of human FcεRI, or with two expression vectors each comprising a nucleic acid molecule encoding human CD303 antigen and the gamma chain of human FcεRI, respectively.

4. The cell line according to claim 1, wherein said cell line has on its surface between 20,000 and 60,000 human CD303 molecules per cell.

5. A method for testing ADCC activity of an antibody against human CD303 antigen, comprising the following steps:
   a) contacting the cell line according to claim 1 with an antibody against human CD303 antigen and effector cells;
   b) incubating the cells obtained in step a) for a suitable time to allow lysis of the cells; and
   c) measuring degree of lysis of the incubated cells.

6. A kit for characterizing anti-CD303 antibodies comprising the cell line according to claim 1.

7. The cell line according to claim 4, wherein said cell line has on its surface between 25,000 and 50,000 human CD303 molecules per cell.

8. The cell line according to claim 2, wherein said cell line has on its surface between 20,000 and 60,000 human CD303 molecules per cell.

9. The cell line according to claim 8, wherein said cell line has on its surface between 25,000 and 50,000 human CD303 molecules per cell.

10. The cell line according to claim 3, wherein said cell line has on its surface between 20,000 and 60,000 human CD303 molecules per cell.

11. The cell line according to claim 10, wherein said cell line has on its surface between 25,000 and 50,000 human CD303 molecules per cell.

12. The method of using the cell line according to claim 5, wherein said activity of an antibody against human CD303 antigen is selected from ADCC, CDC, cytokine secretion, apoptosis or phagocytosis.

13. The method of using the cell line according to claim 5, wherein said human effector cells are from a subject suffering from BPDCN or from an autoimmune disease.

14. The kit according to claim 6, further comprising at least one reagent selected from effector cells, polyvalent IgG, and reference anti-CD303 antibodies.

* * * * *

SEQUENCE LISTING

```
<160> NUMBER OF SEQ ID NOS: 4

<210> SEQ ID NO 1
<211> LENGTH: 1313
<212> TYPE: DNA
<213> ORGANISM: Homo sapiens
<220> FEATURE:
<221> NAME/KEY: misc_feature
<223> OTHER INFORMATION: human CD303

<400> SEQUENCE: 1
cagtgattct cgtgcctcag cctcctgagt agccgaaatt acagacgtgt gccaccatgc      60
ttggctaatt ttttggatttt ttagtagaga tggggtttca ctatgttggc caggctagtc     120
ttgaactcct ggcctgaagc aatccgccca cctcagcctc ccaaagtgct gagattatag     180
gcacgagcca ctacacctgg ccacaaaatt ctttaaagaa gccaatccca tcctccctca     240
agagccaagg ggccacctca ccctcttgtt acagcagatc ctgcctccca cagtcaccct     300
gctcccaagt gcaacctctg tctgaccctg catggtgtgc ggtgccctcc tgcctcaggc     360
cgcgaagaag gatctaaggg cttggcttgt ttgaaagaac cacaccccga aagtaacatc     420
tttggagaaa gtgatacaag agcttctgca cccacctgat agaggaagtc caaagggtgt     480
gcgcacacac aatggtgcct gaagaagagc ctcaagaccg agagaaagga ctctggtggt     540
tccagttgaa ggtctggtcc atggcagtcg tatccatctt gctcctcagt gtctgtttca     600
ctgtgagttc tgtggtgcct cacaattta tgtatagcaa aactgtcaag aggctgtcca     660
agttacgaga gtatcaacag tatcatccaa gcctgaccta cgtcatggaa ggaaaggaca     720
```

| | |
|---|---|
| tagaagattg gagctgctgc ccaaccccct tggacttcat tcagtctagt tgctacttta | 780 |
| tttctactgg gatgcaatct tggactaaga gtcaaaagaa ctgttctgtg atggggctg | 840 |
| atctggtggt gatcaacacc aggaagaac aggatttcat cattcagaat ctgaaaagaa | 900 |
| attcttctta ttttctgggg ctgtcagatc caggggtcg gcgacattgg caatgggttg | 960 |
| accagacacc atacaatgaa atgtcacat tctggcactc aggtgaaccc aataaccttg | 1020 |
| atgagcgttg tgcgataata aatttccgtt cttcagaaga atggggctgg aatgacattc | 1080 |
| actgtcatgt acctcagaag tcaatttgca agatgaagaa gatctacata taaatgaaat | 1140 |
| attctccctg gaaatgtgtt tgggttggca tccaccgttg tagaaagcta aattgatttt | 1200 |
| ttaatttatg tgtaagtttt gtacaaggaa tgcccctaaa atgtttcagc aggctgtcac | 1260 |
| ctattacact tatgatataa tccaaaaaaa aaaaaaaaaa aaaaaaaaaa aaa | 1313 |

```
<210> SEQ ID NO 2
<211> LENGTH: 213
<212> TYPE: PRT
<213> ORGANISM: Homo sapiens
<220> FEATURE:
<221> NAME/KEY: misc_feature
<223> OTHER INFORMATION: human CD303

<400> SEQUENCE: 2

Met Val Pro Glu Glu Pro Gln Asp Arg Glu Lys Gly Leu Trp Trp
1               5                   10                  15

Phe Gln Leu Lys Val Trp Ser Met Ala Val Val Ser Ile Leu Leu
                20                  25                  30

Ser Val Cys Phe Thr Val Ser Val Val Pro His Asn Phe Met Tyr
                35                  40                  45

Ser Lys Thr Val Lys Arg Leu Ser Lys Leu Arg Glu Tyr Gln Gln Tyr
        50                  55                  60

His Pro Ser Leu Thr Cys Val Met Glu Gly Lys Asp Ile Glu Asp Trp
65                  70                  75                  80

Ser Cys Cys Pro Thr Pro Trp Thr Ser Phe Gln Ser Ser Cys Tyr Phe
                85                  90                  95

Ile Ser Thr Gly Met Gln Ser Trp Thr Lys Ser Gln Lys Asn Cys Ser
                100                 105                 110

Val Met Gly Ala Asp Leu Val Val Ile Asn Thr Arg Glu Glu Gln Asp
                115                 120                 125

Phe Ile Ile Gln Asn Leu Lys Arg Asn Ser Ser Tyr Phe Leu Gly Leu
        130                 135                 140

Ser Asp Pro Gly Gly Arg Arg His Trp Gln Trp Val Asp Gln Thr Pro
145                 150                 155                 160

Tyr Asn Glu Asn Val Thr Phe Trp His Ser Gly Glu Pro Asn Asn Leu
                165                 170                 175

Asp Glu Arg Cys Ala Ile Ile Asn Phe Arg Ser Ser Glu Glu Trp Gly
                180                 185                 190

Trp Asn Asp Ile His Cys His Val Pro Gln Lys Ser Ile Cys Lys Met
                195                 200                 205

Lys Lys Ile Tyr Ile
        210

<210> SEQ ID NO 3
<211> LENGTH: 591
<212> TYPE: DNA
<213> ORGANISM: Homo sapiens
<220> FEATURE:
```

<221> NAME/KEY: misc_feature
<223> OTHER INFORMATION: gamma chain of human FcERI receptor

<400> SEQUENCE: 3

```
cagaacggcc gatctccagc ccaagatgat tccagcagtg gtcttgctct tactccttt    60
ggttgaacaa gcagcggccc tgggagagcc tcagctctgc tatatcctgg atgccatcct   120
gtttctgtat ggaattgtcc tcaccctcct ctactgtcga ctgaagatcc aagtgcgaaa   180
ggcagctata accagctatg agaaatcaga tggtgtttac acgggcctga gcaccaggaa   240
ccaggagact tacgagactc tgaagcatga gaaaccacca cagtagcttt agaatagatg   300
cggtcatatt cttctttggc ttctggttct tccagccctc atggttggca tcacatatgc   360
ctgcatgcca ttaacaccag ctggccctac ccctataatg atcctgtgtc ctaaattaat   420
ataccaccagt ggttcctcct ccctgttaaa gactaatgct cagatgctgt ttacggatat  480
ttatattcta gtctcactct cttgtcccac ccttcttctc ttccccattc ccaactccag   540
ctaaaatatg ggaagggaga accccccaata aaactgccat ggactggact c            591
```

<210> SEQ ID NO 4
<211> LENGTH: 86
<212> TYPE: PRT
<213> ORGANISM: Homo sapiens
<220> FEATURE:
<221> NAME/KEY: misc_feature
<223> OTHER INFORMATION: gamma chain of human FcERI receptor

<400> SEQUENCE: 4

```
Met Ile Pro Ala Val Val Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Ala Ile Thr Ser Tyr Glu Lys Ser Asp Gly Val
    50                  55                  60

Tyr Thr Gly Leu Ser Thr Arg Asn Gln Glu Thr Tyr Glu Thr Leu Lys
65                  70                  75                  80

His Glu Lys Pro Pro Gln
                85
```